United States Patent [19]
Patchornik et al.

[11] 3,994,875
[45] Nov. 30, 1976

[54] ANTIBIOTICS

[75] Inventors: Abraham Patchornik, Ness-Ziona; Fortuna Haviv, Rehovot, both of Israel

[73] Assignee: Yeda Research & Development Co. Ltd., Rehovot, Israel

[22] Filed: Dec. 16, 1975

[21] Appl. No.: 641,275

Related U.S. Application Data

[62] Division of Ser. No. 482,264, June 14, 1974, Pat. No. 3,948,904.

[52] U.S. Cl. .......................... 260/239.1; 260/329 S; 260/332.3 R; 260/332.5; 260/508; 260/509; 260/516; 424/246; 424/271

[51] Int. Cl.$^2$ ............... C07D 499/46; C07D 499/48

[58] Field of Search ................................. 260/239.1

[56] References Cited

FOREIGN PATENTS OR APPLICATIONS

| 753,387 | 12/1970 | Belgium | 260/239.1 |
|---|---|---|---|
| 2,203,653 | 8/1972 | Germany | 260/239.1 |

*Primary Examiner*—Gerald A. Schwartz
*Attorney, Agent, or Firm*—L. Ruth Hattan; Eugene O. Retter; George W. Rauchfuss, Jr.

[57] ABSTRACT

Novel cephalosporin and penicillin antibiotic derivatives.

21 Claims, No Drawings

ANTIBIOTICS

This is a division, of application Ser. No. 482,264, filed 6-14-74, now U.S. Pat. No. 3,948,904.

FIELD OF INVENTION

This invention relates to novel cephalosporin and penicillin derivatives useful as antibiotics and processes for their peparation.

SUMMARY OF INVENTION

Compounds of the following general Formula I are useful as antibiotic agents:

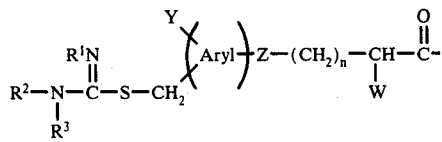

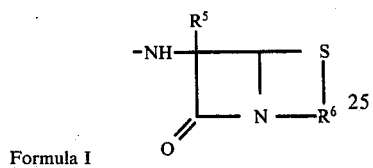

Formula I wherein Aryl is selected from phenyl or 2-thienyl; Y is selected from hydrogen, chlorine, bromine, a straight or branched lower alkyl group of from 1 to 4 carbon atoms, or an alkoxy group of from 1 to 4 carbon atoms with the proviso that when Aryl is 2-thienyl, Y is hydrogen; each of $R^1$, $R^2$ and $R^3$ is selected from hydrogen or a straight or branched lower alkyl group of from 1 to 4 carbon atoms; Z is selected from a bond, oxygen, sulfur or imino with the proviso that when Aryl is 2-thienyl, Z is a bond; W is selected from hydrogen, methyl, amino, hydroxy, $SO_3H$, or $COOR^4$ wherein $R^4$ is selected from hydrogen or 5-indanyl; n is zero, 1 or 2 with the proviso that when W is other than hydrogen or methyl and Z is other than a bond, n is not zero; $R^5$ is selected from hydrogen or methoxy; $R^6$ is selected from the moiety

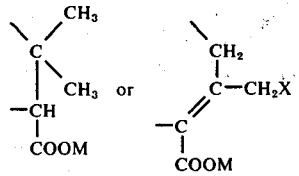

wherein M is selected from hydrogen; a pharmaceutically acceptable non-toxic anion or cation charge; alkanoyloxymethyl wherein the alkanoyl moiety contains from 1 to 5 carbon atoms and may be straight or branched, alkanoylaminomethyl wherein the alkanoyl moiety contains from 1 to 5 carbon atoms and may be straight or branched and wherein the amino nitrogen may be substituted with an alkyl group of from 1 to 4 carbon atoms, alkoxycarbonylaminomethyl wherein the alkoxy moiety contains from 1 to 4 carbon atoms and may be straight or branched and wherein the amino nitrogen may be substituted with an alkyl group of from 1 to 4 carbon atoms, p-(alkanoyloxy)benzyl wherein the alkanoyl moiety contains from 1 to 5 carbon atoms and may be straight or branched or aminoalkanoyloxymethyl wherein the alkanoyl moiety contains from 2 to 15 carbon atoms, and the amino nitrogen may be mono- or disubstituted with a lower alkyl group of from 1 to 4 carbon atoms. X is selected from hydrogen, acetoxy, 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5-ylthio, or 2-methyl-1,3,4-thiadiazol-5-ylthio; and pharmaceutically acceptable salts thereof.

DETAILED DESCRIPTION OF INVENTION

In general Formula I the substituent groups as represented by M in addition to being hydrogen or a pharmaceutically acceptable non-toxic anion or cation charge may also be alkanoyloxymethyl as represented by the structure

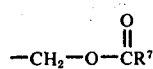

wherein $R^7$ is selected from a straight or branched lower alkyl group of from 1 to 4 carbon atoms; alkanoylaminomethyl or alkoxycarbonylaminomethyl as represented by the structure

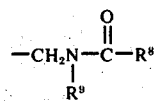

wherein $R^8$ represents a straight or branched lower alkyl group of from 1 to 4 carbon atoms or a straight or branched alkoxy group of from 1 to 4 carbon atoms and $R^9$ represents hydrogen or a lower alkyl group of from 1 to 4 carbon atoms; p-(alkanoyloxy)benzyl as represented by the structure

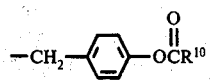

wherein $R^{10}$ is a straight or branched lower alkyl of from 1 to 4 carbon atoms, or aminoalkanoyloxymethyl as represented by the group

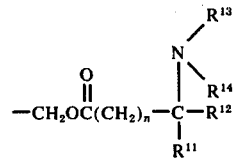

wherein n is 0 to 5, each of $R^{11}$ and $R^{12}$ is selected from hydrogen or lower alkyl of from 1 to 4 carbon atoms, and each of $R^{13}$ and $R^{14}$ is selected from hydrogen or a straight or branched lower alkyl group of from 1 to 4 carbon atoms.

Illustrative examples of straight or branched lower alkyl groups of from 1 to 4 carbon atoms which Y, $R^1$, $R^2$, $R^3$, $R^7$, $R^8$, $R^{10}$, $R^{13}$ and $R^{14}$ may represent are methyl, ethyl, n-propyl, isopropyl, n-butyl and tert-butyl.

Examples of lower alkyl groups of from 1 to 4 carbon atoms which $R^9$, $R^{11}$ and $R^{12}$ may represent are methyl, ethyl, n-propyl and n-butyl.

Examples of lower alkoxy groups which Y may represent are methoxy, ethoxy, n-propoxy and n-butoxy.

Illustrative examples of straight or branched lower alkoxy groups which $R^8$ may represent are methoxy, ethoxy, n-propoxy, isopropoxy, sec-butoxy, and n-butoxy.

In general Formula I the substituent group X may represent in addition to hydrogen or acetoxy, a heterocyclicthio group selected from 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5-ylthio, or 2-methyl-1,3,4-thiadiazol-5-ylthio as represented by the following respective structures:

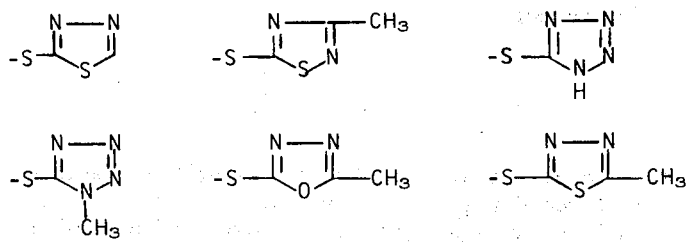

When the Aryl group in the compounds of general Formula I represents phenyl, each of the isothioureamethyl substituent and the Y substituent may be individually attached to any of the positions 2 through 6 of the phenyl ring. Compounds of this type may be represented by the following general Formula II.

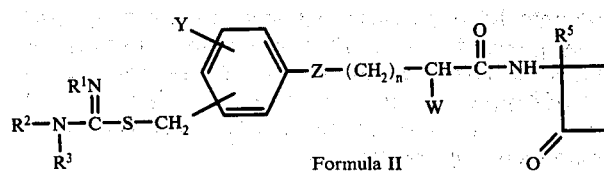

Formula II

The preferred positions of attachment of the isothioureamethyl substituent in the above Formula II are the ortho- and para- positions of the phenyl ring. In the above Formula II the substituents as represented by Y, $R^1$, $R^2$, $R^3$, Z, $n$, W, $R^5$ and $R^6$ have the meanings defined in general Formula I.

When the Aryl group in the compounds of general Formula I represents 2-thienyl, Y is hydrogen, and Z is a bond. Compounds of this type may be represented by the following Formula III

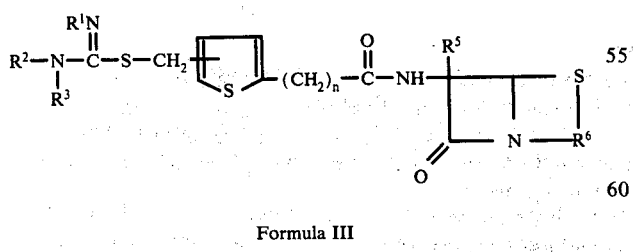

Formula III

In the compounds of the above Formula III the isothiourea substituent group may be attached at the 4 or 5 position of the thienyl group. In the above Formula III the substituents as represented by $R^1$, $R^2$, $R^3$ $n$, W, $R^5$ and $R^6$ have the meanings defined in general Formula I.

It is apparent from the foregoing description of general Formula I that the compounds of this invention are either penicillin derivatives when $R^6$ represents the moiety

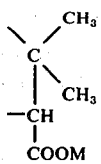

or cephalosporin derivatives when $R^6$ represents the moiety

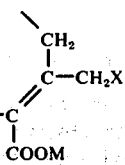

wherein M and X have the meanings defined in general Formula I.

The cephalosporin derivatives which represent a preferred embodiment of this invention may be represented by the following Formula IV.

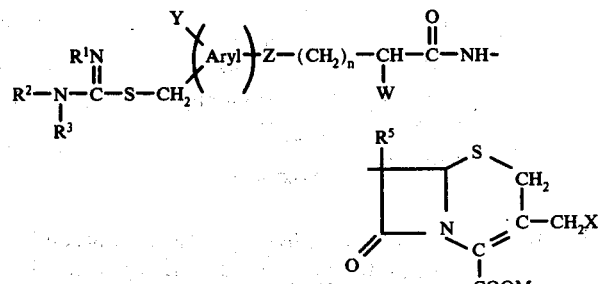

Formula IV wherein Aryl is selected from phenyl or 2-thienyl; Y is selected from hydrogen, chlorine, bromine, a straight or branched lower alkyl group of from 1 to 4 carbon atoms, or an alkoxy group of from 1 to 4 carbon atoms, with the proviso that when Aryl is 2-thienyl, Y is hydrogen; each of $R^1$, $R^2$ and $R^3$ is selected from hydrogen or a straight or branched lower alkyl group of from 1 to 4 carbon atoms; Z is selected from a bond, oxygen, sulfur or imino with the proviso that when Aryl is 2-thienyl, Z is a bond; W is selected from hydrogen, methyl, amino, hydroxy, $SO_3H$, or $COOR^4$ wherein $R^4$ is selected from hydrogen or 5-indanyl; $n$ is zero, 1 or 2 with the proviso that when W is other than hydrogen or methyl, and Z is other than a bond, n is not zero; $R^5$ is selected from hydrogen or methoxy; M is selected from hydrogen, a pharmaceutically acceptable non-toxic anion or cation charge, alkanoyloxy methyl wherein the alkanoyl moiety contains from 1 to 5 carbon atoms and may be straight or branched, alkanoylaminomethyl wherein the alkanoyl moiety contains from 1 to 5 carbon atoms and may be straight or branched and wherein the amino nitrogen may be substituted with an alkyl group of from 1 to 4 carbon atoms, alkoxycarbonylaminomethyl wherein the alkoxy moiety contains from 1 to 4 carbon atoms and may be straight or branched and wherein the amino nitrogen may be substituted with an alkyl group of from 1 to 4 carbon atoms, p-(alkanoyloxy)benzyl wherein the alkanoyl moiety contains from 1 to 5 carbon atoms and may be straight or branched; or aminoalkanoyloxymethyl wherein the alkanoyl moiety contains from 2 to 15 carbon atoms and the amino nitrogen may be mono- or disubstituted with a lower alkyl group of from 1 to 4 carbon atoms; X is selected from hydrogen, acetoxy, 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5-ylthio, or 2-methyl-1,3,4-thiadiazol-5-ylthio; and pharmaceutically acceptable salts thereof.

The penicillin derivatives which represent a preferred embodiment of this invention may be represented by the following formula V:

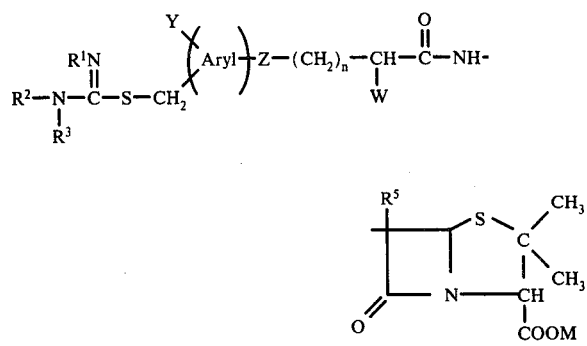

Formula V wherein Aryl is phenyl or 2-thienyl; Y is selected from hydrogen, chlorine, bromine, a straight or branched lower alkyl group of from 1 to 4 carbon atoms, or an alkoxy group of from 1 to 4 carbon atoms with the proviso that when Aryl is 2-thienyl, Y is hydrogen; each of $R^1$, $R^2$ and $R^3$ is selected from hydrogen or a lower alkyl group of from 1 to 4 carbon atoms; Z is selected from a bond, oxygen, sulfur or imino with the proviso that when Aryl is 2-thienyl, Z is a bond; W is selected from hydrogen, methyl, amino, hydroxy, $SO_3H$ or $COOR^4$ wherein $R^4$ is selected from hydrogen or 5-indanyl; n is zero, 1 or 2 with the proviso that when W is other than hydrogen or methyl and Z is other than a bond, n is not zero; $R^5$ is selected from hydrogen or methoxy; M is selected from hydrogen, a pharmaceutically acceptable non-toxic anion or cation charge, alkanoyloxymethyl wherein the alkanoyl moiety contains from 1 to 5 carbon atoms and may be straight or branched, alkanoylaminomethyl wherein the alkanoyl moiety contains from 1 to 5 carbon atoms and may be straight or branched and wherein the amino nitrogen may be substituted with an alkyl group of from 1 to 4 carbon atoms, alkoxycarbonylaminomethyl wherein the alkoxy moiety contains from 1 to 4 carbon atoms and may be straight or branched and wherein the amino nitrogen may be substituted with an alkyl group of from 1 to 4 carbon atoms, p-(alkanoyloxy)benzyl wherein the alkanoyl moiety contains from 1 to 5 carbon atoms and may be straight or branched; or aminoalkanoyloxymethyl wherein the alkanoyl moiety contains from 2 to 15 carbon atoms, and the amino nitrogen may be mono- or di-substituted with a lower alkyl group of from 1 to 4 carbon atoms; and pharmaceutically acceptable salts thereof.

In the compounds of Formulas IV and V it is apparent that the $R^5$ substituent may be either cis or trans to the hydrogen atom at the 6-position of the cephalosporin in derivatives of Formula IV and at the 5-position of the penicillin derivatives of Formula V. The compounds of Formulas IV and V wherein the $R^5$ substituent is cis to the aforementioned hydrogen atoms are preferred.

Other preferred embodiments of this invention are: (A) compounds wherein W represents hydrogen, hydroxy, amino, $SO_3H$, and $COOR^4$ wherein $R^4$ represents hydrogen in that such substitution results in compounds having broader spectrum of activity and/or improved oral activity for example compounds wherein 1. W represents hydroxy are more resistant to β-lactamase organisms;
2. W represents $SO_3H$ or $COOR^4$ wherein $R^4$ represents hydrogen have broader gram negative spectrum;
3. W represents $NH_2$ have improved oral activity; (B) compounds wherein $R^5$ represents methoxy are of particular interest in that such compounds demonstrate antibacterial activity against cephalosporinase producing gram negative organisms.

C. compounds wherein X represents acetoxy, 2-methyl-1,3,4-thiadiazol-5-ylthio or 1-methyltetrazol-5l-ylthio.

Of the preferred embodiments set forth in (A), (B) and (C) compounds wherein Z represents a bond, are more preferred.

The most preferred compounds of this invention are those represented by the following Formula VI

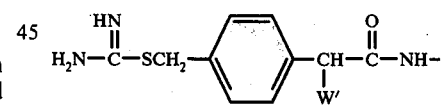

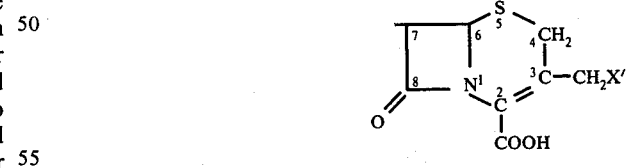

Formula VI wherein W' is selected from hydrogen, hydroxy, amino, COOH or $SO_3H$; X' is selected from hydrogen, acetoxy, 2-methyl-1,3,4-thiadiazol-5-ylthio or 1-methyltetrazol-5-ylthio; and pharmaceutically acceptable salts thereof.

In the above Formula VI compounds wherein the hydrogen atoms at the 6- and 7- positions are cis to one another are preferred.

The individual optical isomers of the compounds of this invention wherein W is other than hydrogen are also included within the scope of this invention.

The non-toxic acid addition salts of the compounds of this invention such as mineral acid addition salts, for example, hydrogen chloride, hydrogen bromide, hydrogen iodide, sulfate, sulfamate and phosphate and organic acid addition salts, for example, maleate, acetate, citrate, oxalate, succinate, benzoate, tartrate, fumarate, malate, mandelate and ascorbate, are also included within the scope of this invention.

Also within the scope of this invention are the non-toxic pharmaceutically acceptable salts of the compounds of this invention wherein W represents COOH or $SO_3H$ and compounds wherein M represents hydrogen. Illustrative pharmaceutically acceptable salts of these acid derivatives are primary, secondary or tertiary amines, for example, cyclohexylamine, ethylamine and pyridine.

The pharmaceutically acceptable cations which may be present as the group M in the compounds of general Formulas I to VI include alkali metal ions, for example sodium ion, potassium ion, calcium ion as well as ammonium, and organic amine cations, for example, lower alkyl ammonium groups, such as triethylammonium, and N-ethylpiperidine.

The salt forms of compounds of Formulas I to VI wherein M is a pharmaceutically acceptable cation are prepared in the manner recognized in the art and may be formed in situ or by reacting the corresponding acid with base for example sodium bicarbonate or triethylamine.

The compounds of this invention may be administered in a manner similar to that of many well known cephalosporin compounds, for example, cephalexin, cephalothin, or cephaloglycine. They may be administered alone or in the form of pharmaceutical preparations either orally, parenterally and topically to warm blooded animals, that is, birds and mammals, for example, cats, dogs, cattle, and horses, and humans. For oral administration the compounds may be administered in the form of tablets, capsules or pills or in the form of elixirs or suspensions. For parenteral administration they are best used in the form of a sterile aqueous solution which may contain other solutes, for example, enough saline or glucose to make the solution isotonic. For topical administration the compounds may be incorporated into creams or ointments.

Illustrative examples of bacteria against which the compounds of this invention are active are *Staphylococcus aureus*, *Salmonella schottmuelleri*, *Klebsiella pneumoniae*, *Diplococcus pneumonia*, and *Streptococcus pyogenes*.

An illustrative example of a cephalosporin derivative of this invention is 3-[(acetyloxy)methyl]-7-[[2-[4-(isothioureamethyl)phenyl]acetyl]amino]-8-oxo-5-thia-1-azabicyclo[4.2.0]oct-2-ene-2-carboxylic acid. An illustrative example of a penicillin derivative of this invention is 6-[[2-[4-(isothioureamethyl)phenyl]acetyl]amino]-3,3-dimethyl-7-oxo-4-thia-1-azabicyclo[3.2.0]heptane-2-carboxylic acid. Additional examples of compounds of this invention are set forth hereinbelow in the specific compounds which are representative of the invention.

The compounds of Formula I wherein $R^4$ is hydrogen may be prepared by treating a derivative of the formula

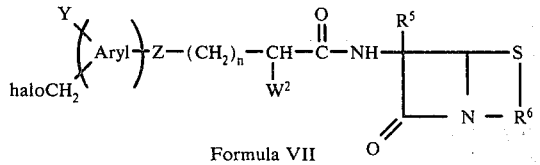

Formula VII with a derivative of the formula

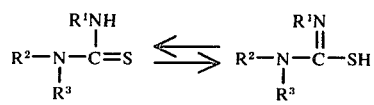

Formula VIII wherein Aryl is selected from phenyl or 2-thienyl; halo is selected from chlorine or bromine; Y is selected from hydrogen, chlorine, bromine, a straight or branched lower alkyl group of from 1 to 4 carbon atoms, or an alkoxy group of from 1 to 4 carbon atoms with the proviso that when Aryl is 2-thienyl, Y is hydrogen; Z is selected from a bond, oxygen, sulfur, or imino with the proviso that when Aryl is 2-thienyl, Z is a bond; $W^2$ is selected from hydrogen, methyl, amino, hydroxy, $SO_3H$ or COOH; n is zero, 1 or 2 with the proviso that when $W^2$ is other than hydrogen or methyl and Z is other than a bond, n is not zero; $R^5$ is selected from hydrogen or methoxy; $R^6$ is selected from the moiety

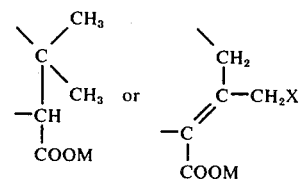

wherein M is selected from hydrogen; a pharmaceutically acceptable non-toxic anion or cation charge; alkanoyloxymethyl wherein the alkanoyl moiety contains from 1 to 5 carbon atoms and may be straight or branched, alkanoylaminomethyl wherein the alkanoyl moiety contains from 1 to 5 carbon atoms and may be straight or branched and wherein the amino nitrogen may be substituted with an alkyl group of from 1 to 4 carbon atoms, alkoxycarbonylaminomethyl wherein the alkoxy moiety contains from 1 to 4 carbon atoms and may be straight or branched and wherein the amino nitrogen may be substituted with an alkyl group of from 1 to 4 carbon atoms, p-(alkanoyloxy)benzyl wherein the alkanoyl moiety contains from 1 to 5 carbon atoms and may be straight or branched or aminoalkanoyloxymethyl wherein the alkanoyl moiety contains from 2 to 15 carbon atoms, and the amino nitrogen may be mono- or disubstituted with a lower alkyl group of from 1 to 4 carbon atoms; X is selected from hydrogen, acetoxy, 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5-ylthio, or 2-methyl-1,3,4-thiadiazol-5-ylthio; each of $R^1$, $R^2$ and $R^3$ is selected from hydrogen or a straight or branched lower alkyl group of from 1 to 4 carbon atoms.

The above reaction is carried out in an alcoholic solvent at temperatures of from 0° C to 100° C, preferably from 25° to 50° C, for from ½ hour to 6 hours yielding the corresponding isothiouronium hydrochloride derivative in solution. The organic solvent is evaporated, and the residual oil is triturated with appropriate organic solvents such as ether, hexane, ethyl acetate or acetonitrile, to give the isothioureamethyl substituted compound.

When the substituent group $W^2$ in the above Formula VII represents an amino group, suitable blocking groups, e.g., an acid salt such as hydrochloride salt, an acyl group, or tert-butoxycarbonyl may be employed to protect the amino function. Such blocking groups are removed after the coupling reaction by methods generally known in the art, e.g., as described by Lemieux et al., in U.S. Pat. No. 3,657,232.

Illustrative examples of compounds of Formula VIII are isothiourea, 1-ethyl-3-n-propylisothiourea, 1-ethyl-3-n-butylisothiourea, 1,1-di-n-propyl-3-ethylisothiourea, 1-ethyl-3-isopropylisothiourea, 1,1,3-triethylisothiourea, 1,1-di-n-propyl-3-methylisothiourea, 1,3-di-sec-butylisothiourea, 1,3-di-n-propylisothiourea, 1-n-butyl-3-methylisothiourea, 1-ethyl-3-methylisothiourea, 1,1-diethyl-3-methylisothiourea, 1,3-diethylisothiourea, 1-ethylisothiourea, 3-n-propylisothiourea, 1,3-dimethylisothiourea, 1,3-diisopropylisothiourea, 1,3-di-n-butylisothiourea, 1-methyl-3-ethylisothiourea, and 1,1-dimethyl-3-ethylisothiourea.

Compounds of general Formula VII may be prepared by coupling a derivative of the formula

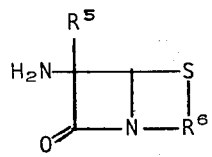

Formula IX with an acid of the formula

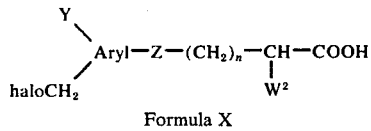

Formula X or a functional derivative thereof wherein Aryl, halo, Y, Z, n, $W^2$, $R^5$ and $R^6$ have the meanings defined in general Formula VII.

When the substituent group $W^2$ in the above Formula X represents an amino group suitable blocking groups, e.g., an acid salt such as hydrochloride salt, tert-butoxycarbonyl, or carbobenzyloxy are employed to protect the amino function in a manner similar to that described hereinabove.

Functional equivalents of the acids as represented by Formula X include the acid halides, for example, the acid chloride, acid anhydrides, including mixed anhydrides with, for example, alkylphosphoric acids, lower aliphatic monoesters of carbonic acid, or alkyl or aryl sulfonic acids. Additionally, the acid azide or an active ester or thioester, for example, with p-nitrophenol, 2,4-dinitrophenol, or thioacetic acid, may be used, or the free acid as represented by Formula X may be coupled with the 7-aminocephalosporanic acid derivative or a 6-aminopenicillanic acid derivative as represented by Formula VIII after first reacting the acid with N,N'-dimethylchloroforminium chloride or by use of a carbodiimide reagent, for example, N,N'-diisopropylcarbodiimide, N,N'-dicyclohexylcarbodiimide, or N-cyclohexyl-N'-(2-morpholinoethyl)carbodiimide.

The coupling reaction is generally carried out in the presence of a solvent. Suitable solvents include ethyl acetate, acetone, dioxane, acetonitrile, chloroform, methylene chloride, tetrahydrofuran and dimethyl formamide. As hydrophilic solvents are employed mixtures of these solvents with water are also suitable for the above reaction. The coupling reaction may be carried out in the presence of a base, for example, an alkaline bicarbonate. The temperature of the reaction may vary from $-10°$ to $100°$ C, and the reaction time may vary from about ½ hour to 10 hours. The cephalosporin products are isolated by conventional methods.

The compounds of general Formula VII may also be prepared by combining a modified polystyrene containing nitrophenol or hydroxysuccinimide groups with an acid of general Formula X and mixing the activated acid thus formed with a compound of general Formula IX by the general procedure described in Canadian Patent No. 892,580, issued Feb. 8, 1972, by substituting a compound of general Formula IX for the penicillanic acid derivatives described therein.

The compounds of Formula IX may be more fully described by the following Formulas XI and XII

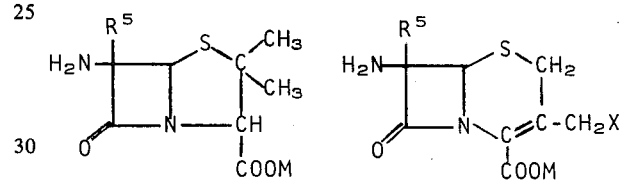

Formula XI  Formula XII wherein $R^5$, M and X have the meanings defined in Formula I. Compounds of Formulas XI and XII wherein $R^5$ is hydrogen, M is hydrogen or a pharmaceutically acceptable non-toxic anion or cation and X is hydrogen or acetoxy are commercially available or may be prepared by methods well known in the art. The corresponding compounds wherein $R^5$ is methoxy may be prepared by the general procedures described in U.S. Pat. No. 3,778,432.

Compounds of Formulas XI and XII wherein M is alkanoyloxymethyl may be prepared by reacting the corresponding acid in the form of a salt, such as an alkali metal salt or the triethylammonium salt with a compound of the formula

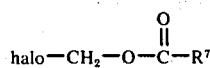

wherein halo is chlorine or bromine and $R^7$ is a straight or branched lower alkyl group of from 1 to 4 carbon atoms by the general procedure described in U.S. Pat. No. 3,655,658.

Compounds of Formulas XI and XII wherein M is alkanoylaminomethyl or alkoxycarbonylaminomethyl are prepared by treating the sodium salt of acid derivatives of Formula XI and XII in an organic solvent such as dimethyl formamide or hexamethylphosphoramide, at room temperature with an equivalent amount of an alkanoylaminomethyl halide or an alkoxycarbonylaminomethyl halide for ½ to 3 hours after which the mixture is poured into ice-water. The resulting precipitated product is isolated by standard procedures.

Compounds of Formulas XI and XII wherein M is p-(alkanoyloxy)benzyl are prepared by adding 2-equivalents of the p-(alkanoyloxy)benzyl alcohol to a suspension of the sodium salt of acid derivatives of Formulas XI and XII in dimethyl formamide or hexamethylphosphoramide after which the mixture is cooled to 0° C. 1.2 equivalents of dicyclohexylcarbodiimide in dimethyl formamide is added dropwise to the mixture with stirring. The mixture is stirred at 0° C for ½ to 3 hours and then an additional 2 to 5 hours at room temperature. The formed dicyclohexylurea is removed by filtration and the filtrate is diluted with chloroform, methylene chloride, or ethyl acetate, washed with water and dried to give the product.

Compounds of Formulas XI and XII wherein M is aminoalkanoyloxymethyl are prepared by mixing a suspension of the sodium salt of an acid of Formula XI and XII and an excess of an appropriate amine protected aminoalkanoyloxymethyl halide in a solvent such as dimethyl formamide, hexamethylphosphoramide or dimethyl sulfoxide for 2 to 96 hours. The mixture is then diluted with a solvent such as ethyl acetate or methylene chloride, washed with water, aqueous base, then water. The organic phase is separated and the precipitate isolated by conventional means followed by deprotection of the amine group to give the product.

Compounds of Formula XII wherein X is a heterocyclicthio group as described in Formula VI are prepared by dissolving 1 equivalent of the acid in the form of a salt, such as, the sodium salt wherein X is acetoxy in about 500 to 2000 ml of water at from 50° to 80° C under a nitrogen atmosphere and subsequently adding 1 equivalent of a base, such as, triethylammonium or sodium bicarbonate and 1 to 3 equivalents of the heterocyclic-thiol. The reaction mixture is stirred at 50° to 90° C for about 2 to 6 hours after which the water is evaporated, and the residue is taken up in an organic solvent, such as, methanol, ethanol, or dimethyl formamide, and precipitated with an organic solvent, such as, acetonitrile, acetone, ethyl acetate or chloroform.

In a similar manner the cephalosporin in derivatives of this invention wherein X represents a heterocyclicthio group selected from 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5-ylthio, or 2-methyl-1,3,4-thiadiazol-5-ylthio and M represents hydrogen may be prepared by reacting the 3-[(acetyloxy)methyl]-derivative with the appropriate heterocyclicthiol group as represented by the following:

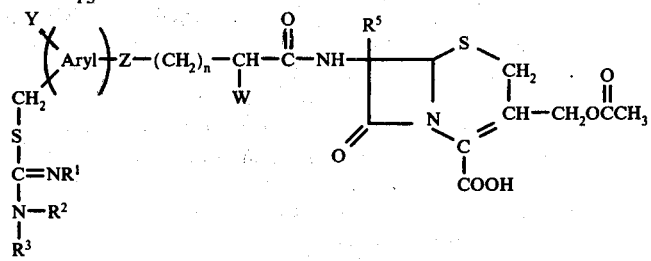

Formula XV

+

H-S-hetero

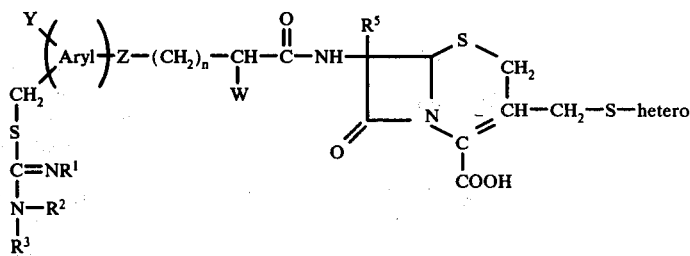

Formula XVI

In the above Formulas XV and XVI Aryl is selected from phenyl or 2-thienyl; Y is selected from hydrogen, chlorine, bromine, a straight or branched lower alkyl group of from 1 to 4 carbon atoms, or an alkoxy group of from 1 to 4 carbon atoms with the proviso that when Aryl is 2-thienyl, Y is hydrogen; each of $R^1$, $R^2$ and $R^3$ is selected from hydrogen or a straight or branched lower alkyl group of from 1 to 4 carbon atoms; Z is selected from a bond, oxygen, sulfur or imino with the proviso that when Aryl is 2-thienyl, Z is a bond; W is selected from hydrogen, methyl, amino, hydroxy, $SO_3H$, or $COOR^4$ wherein $R^4$ is selected from hydrogen or 5-indanyl; n is zero, 1 or 2 with the proviso that when W is other than hydrogen or methyl and Z is other than a bond, n is not zero; $R^5$ is selected from hydrogen or methoxy; and the moiety -S-hetero is selected from 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5-ylthio, or 2-methyl-1,3,4-thiadiazol-5-ylthio.

In the above reaction one equivalent of the sodium salt derivative is dissolved in water at a temperature of from 25° to 90° C under a nitrogen atmosphere followed by the addition of one equivalent of a base such as triethylammonium or sodium bicarbonate and from one to three equivalents of the heterothiol derivative after which the reaction mixture is stirred for about 2 to 6 hours at a temperature of from 25° to 90° C.

The compounds of Formula X are prepared by direct halomethylation as described hereinbelow of an acid of the formula

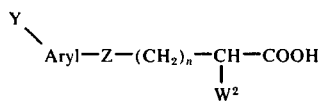

Formula XIII wherein Aryl, Y, Z, n and $W^a$ have the meanings defined in Formula VII which are commercially available or are obtained by methods well known in the art.

When the substituent group $W^2$ in compounds of Formula XIII represents amino, the amino group is protected by a suitable blocking group, for example an acyl group, such as, acetyl or trifluoroacetyl, prior to the halomethylation reaction. Upon completion of the halomethylation reaction the blocking groups may be removed by acid hydrolysis by procedures known in the art.

The halomethylated derivatives of the compounds of Formula XIII are obtained by several methods. For example, a compound of Formula XIII with a source of formaldehyde such as paraformaldehyde, $ClCH_2OCH_3$, or formalin solution, in the presence of a Lewis acid, such as $ZnCl_2$, $AlCl_3$, $SnCl_4$, or $ClSO_3H$ in a solvent, such as petroleum ether, chloroform, carbon tetrachloride, or benzene at a temperature ranging from $-10°$ to $100°$ C during which time hydrogen chloride gas or hydrogen bromide gas is bubbled into the reaction mixture, compounds of general Formula X are obtained.

The reaction of an acid Formula XIII with 34–38% formalin in concentrated hydrochloric acid at temperatures ranging from $-10°$ to $100°$ C during which time hydrogen chloride gas or hydrogen bromide gas is bubbled through the reaction mixture also yields compounds of general Formula X.

Additionally upon reaction of an acid of Formula XIII with trioxane in acetic acid or phosphoric acid at temperatures of from $-10°$ to $100°$ C during which time hydrogen bromide or hydrogen chloride gas is bubbled through the reaction mixture, compounds of general Formula X are obtained. Or, the reaction of an acid of Formula XIII in the presence of a Lewis acid, such as those described hereinabove, with chloromethyl ether at temperatures from $-10°$ and $100°$ C, or the reaction of the acid in acetic acid or concentrated sulfuric acid with dichloromethyl ether in the presence of zinc chloride will give compounds of general Formula X.

The compounds of Formula X wherein $W^2$ represents COOH, and Aryl is phenyl are preferably obtained by treating the corresponding diethyl ester of Formula XIII with 40% formalin in the presence of anhydrous zinc chloride in benzene at about 50° C during which time hydrogen chloride or hydrogen bromide gas is bubbled into the reaction mixture followed by acid hydrolysis.

Compounds of Formula X wherein $W^2$ represents $SO_3H$ may be obtained by the halomethylation reactions described above using an acid of Formula XIII wherein $W^2$ represents $SO_3H$ or the carboxy methyl ester thereof in which latter case the resulting halomethylated compound is converted to the free COOH by acid hydrolysis.

In the halomethylation of compounds of Formula XIII wherein $W^2$ represents OH it may be advantageous to protect the OH group prior to halomethylation as described by V. Reichert, et al., Pharmazie 5, 10 (1950).

The compounds of this invention wherein $R^4$ is hydrogen may also be prepared by coupling a derivative of the formula

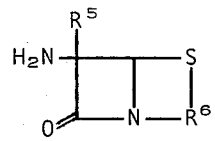

Formula IX with an acid of the formula

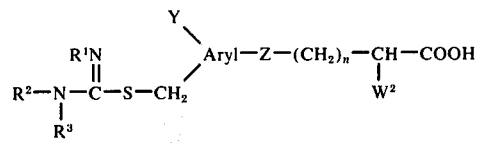

Formula XIV or a functional derivative thereof wherein $R^5$ is selected from hydrogen or methoxy; $R^6$ is selected from the moiety

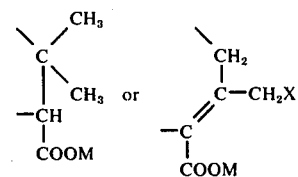

wherein M is selected from hydrogen; a pharmaceutically acceptable non-toxic anion or cation charge; alkanoyloxymethyl wherein the alkanoyl moiety contains from 1 to 5 carbon atoms and may be straight or branched, alkanoylaminomethyl wherein the alkanoyl moiety contains from 1 to 5 carbon atoms and may be straight or branched and wherein the amino nitrogen may be substituted with an alkyl group of from 1 to 4 carbon atoms, alkoxycarbonylaminomethyl wherein the alkoxy moiety contains from 1 to 4 carbon atoms and may be straight or branched and wherein the amino nitrogen may be substituted with an alkyl group of from 1 to 4 carbon atoms, p-(alkanoyloxy)benzyl wherein the alkanoyl moiety contains from 1 to 5 carbon atoms and may be straight or branched or aminoalkanoyloxymethyl wherein the alkanoyl moiety contains from 2 to 15 carbon atoms, and the amino nitrogen may be mono- or disubstituted with a lower alkyl group of from 1 to 4 carbon atoms; X is selected from hydrogen, acetoxy, 1,3,4-thiadiazol-5-ylthio, 3-methyl-1,2,4-thiadiazol-5-ylthio, tetrazol-5-ylthio, 1-methyltetrazol-5-ylthio, 2-methyl-1,3,4-oxadiazol-5-ylthio, or 2-methyl-1,3,4-thiadiazol-5-ylthio; Aryl is selected from phenyl or 2-thienyl; Y is selected from hydrogen, chlorine, bromine, a straight or branched lower alkyl group of from 1 to 4 carbon atoms, or an alkoxy group of from 1 to 4 carbon atoms with the proviso that when Aryl is 2-thienyl, Y is hydrogen; each of $R^1$, $R^2$ and $R^3$ is selected from hydrogen or a straight or branched lower alkyl group of from 1 to 4 carbon atoms; Z is selected from a bond, oxygen, sulfur or imino with the proviso that when Aryl is 2-thienyl, Z is a bond; $W^2$ is selected from hydrogen, methyl, amino, hydroxy, $SO_3H$, or COOH; n is zero, 1 or 2 with the proviso that when $W^2$ is other than hydrogen or methyl and Z is other than a bond, n is not zero.

When the substituent group $W^2$ in the above Formula XIV represents an amino group suitable blocking groups, e.g., a mineral salt such as hydrochloride salt, tert-butoxycarbonyl, or carbobenzyloxy are employed to protect the amino function in a manner similar to that described hereinabove.

Functional equivalents of the acids as represented by Formula XIV include the acid halides, for example, the acid chloride, acid anhydrides, including mixed anhydrides with, for example, alkylphosphoric acids, lower aliphatic mono-esters of carbonic acid, or alkyl or aryl sulfonic acids. Additionally, the acid azide or an active ester or thio-ester, for example, with p-nitrophenol, 2,4-dinitrophenol, or thioacetic acid, may be used, or the free acid as represented by Formula XIV may be coupled with the 7-aminocephalosporanic acid derivative or a 6-aminopenicillanic acid derivative as represented by Formula IX after first reacting the acid with N,N'-dimethylchloroforminium chloride or by use of a carbodiimide reagent, for example, N,N'-diisopropylcarbodiimide, N,N'-dicyclohexylcarbodiimide, or N-cyclohexyl-N'-(2-morpholinoethyl)carbodiimide.

The coupling reaction is generally carried out in the presence of a solvent. Suitable solvents include ethyl acetate, acetone, dioxane, acetonitrile, chloroform, methylene chloride, tetrahydrofuran and dimethylformamide. As hydrophilic solvents are employed mixtures of these solvents with water are also suitable for the above reaction. The coupling reaction is generally carried out in the presence of a base, for example, an alkaline bicarbonate. The temperature of the reaction may vary from −10° to 100° C, and the reaction time may vary from about ½ hour to 10 hours. The cephalosporin products are isolated by conventional methods.

The preparation of compounds of Formula IX is described hereinabove.

Compounds of Formula I wherein $R^4$ is 5-indanyl are prepared by reacting the corresponding acid, that is, compounds of Formula I wherein $R^4$ is hydrogen with 5-indanol in an inert solvent in the presence of N,N'-dicyclohexylcarbodiimide at a pH of about 2.5 and a temperature of from 20° to 30° C. Equimolar amounts of the reactants are employed or a slight excess of the 5-indanol may be used. The molar amount of N,N'-dicyclohexylcarbodiimide employed is equivalent to the molar amount of 5-indanol. Suitable solvents for the reaction are dioxane, tetrahydrofuran, ethyl acetate, dimethyl formamide and methylene chloride.

Compounds of Formula I wherein M represents alkanoylaminomethyl or alkoxycarbonylaminomethyl and W is other than COOH may also be prepared by reacting the corresponding acid in the form of a salt such as an alkali metal salt, for example, the sodium salt with 1.5 to 2.5 equivalents of an appropriate alkanoylaminomethyl halide or alkoxycarbonylaminomethyl halide each of which may be represented by the structure

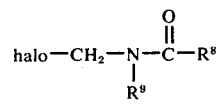

wherein halo is selected from a reactive halogen atom such as chlorine or bromine, $R^8$ is selected from a straight or branched lower alkyl group of from 1 to 4 carbon atoms or a straight or branched lower alkoxy group of from 1 to 4 carbon atoms, and $R^9$ is hydrogen or a lower alkyl group of from 1 to 4 carbon atoms. The reactants are stirred for about 1 to 5 hours in dimethyl formamide, hexamethylphosphoramide or a similar solvent at a temperature ranging from 10° to 45° C after which the reaction mixture is poured into ice water and decanted. The oily residue is taken up in an organic solvent such as ethyl acetate, methylene chloride or benzene, washed with base then with water and dried over magnesium sulfate. The organic solution is evaporated to dryness in vacuo to give the desired ester.

Prior to the above esterification reaction compounds wherein W represents amino are protected with blocking groups, for example, tert-butoxycarbonyl or carbobenzyloxy, such groups being removed upon completion of the esterification procedure by methods generally known in the art, for example, by the method set forth in the aforementioned U.S. Pat. No. 3,657,232.

Compounds of Formula I wherein M represents p-(alkanoyloxy)benzyl and W is other than COOH may also be prepared by reacting molar equivalents of the corresponding acid and a p-(alkanoyloxy)benzyl alcohol wherein the alkanoyl moiety contains from 1 to 4 carbon atoms and may be straight or branched. The reactants are dissolved in an organic solvent such as dimethyl formamide or hexamethylphosphoramide and cooled to a temperature of from −15° C to 25° C after which an equivalent quantity of dicyclohexylcarbodiimide in dimethyl formamide or hexamethylphosphoramide is added dropwise to the reaction mixture with stirring. Stirring is continued for ½ to 2 hours at temperatures of from −15° C to 25° C and then 4 to 6 hours at from 25° to 45° C. The formed dicyclohexylurea is removed by filtration, and the filtrate is diluted with chloroform, ethyl acetate or methylene chloride and washed with water. The organic layer is dried and evaporated to give the product.

Compounds of Formula I wherein M is alkanoyloxymethyl and W is other than COOH may also be prepared by reacting the corresponding acid in the form of a salt, such as an alkali metal salt or the triethylammonium salt with a compound of the formula

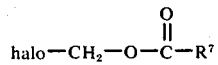

wherein halo is chlorine or bromine, and $R^7$ is a straight or branched lower alkyl group of from 1 to 4 carbon atoms by the general procedure described in U.S. Pat. No. 3,655,658.

Compounds of Formula I wherein M is aminoalkanoyloxymethyl and W is other than COOH may also be prepared by mixing a suspension of the sodium salt of the corresponding acid and an excess of an appropriate amine protected aminoalkanoyloxymethyl halide in a solvent such as dimethyl formamide, hexamethylphosphoramide or dimethyl sulfoxide for 2 to 96 hours. The mixture is then diluted with a solvent such as ethyl acetate or methylene chloride, washed with water, aqueous base, then water. The organic phase is separated and the precipitate isolated by conventional means followed by deprotection of the amine group to give the product.

Compounds of Formula XIV may be prepared by reacting derivatives of Formulas VIII and X by the procedure described on page 14 at lines 9 to 16 and these compounds, particularly those wherein $W^2$ is other than H or $CH_3$ are useful in the preparation of compounds of Formula I.

EXAMPLE 1 p-Chloromethylphenylacetyl chloride

A. At a temperature of from −10° to 0° C hydrogen chloride gas is bubbled through a stirred mixture of 102 g of phenylacetic acid, 67.5 g of paraformaldehyde and 67.5 g of zinc chloride in 1000 ml of petroleum ether for one hour. Stirring is continued for about one hour at room temperature after which the mixture is refluxed for about 2 hours during which time hydrogen chloride gas is bubbled into the mixture. To the reaction mixture is added 1000 ml each of methylene chloride and water. The organic phase is separated and the aqueous phase is extracted twice with methylene chloride. The combined organic phases are extracted four times with a saturated sodium bicarbonate solution. The organic neutral phase is dried over anhydrous sodium sulfate, filtered and the solvent is removed under vacuum to give a neutral by-product which is further identified in Example 5 below. The basic aqueous phase is separated and acidified with cold concentrated hydrochloric acid to pH 2–3, then extracted three times with methylene chloride. The methylene chloride fraction is dried over anhydrous sodium sulfate, filtered and the solvent evaporated. The resulting oily acidic product is chromatographed on silica gel using benzene and benzene-acetone as the eluant to give p-chloromethylphenylacetic acid which is recrystallized from hot chloroform. M.P. 147°–149° C.

B. A mixture of 1 g of p-chloromethylphenylacetic acid and 6 ml of thionyl chloride is stirred at room temperature for 25 hours after which the excess thionyl chloride is removed under vacuum to yield p-chloromethylphenylacetyl chloride.

When in Example 1 (A) an acid selected from Table I is substituted for phenylacetic acid the respective chloromethyl derivative listed in Table I is obtained which can be converted to the acid chloride by the procedure of Example 1 (B).

TABLE I

| Acid | Chloromethyl derivative |
| --- | --- |
| hydrotropic acid | p-chloromethylhydrotropic acid |
| mandelic acid | p-chloromethylmandelic acid |
| dihydrocinnamic acid | p-chloromethyldihydrocinnamic acid |
| 2-methylhydrocinnamic acid | p-chloromethyl-2-methylhydrocinnamic acid |
| 3-phenyllactic acid | 3-(p-chloromethylphenyl)lactic acid |
| 4-phenylbutyric acid | 4-(p-chloromethylphenyl)butyric acid |
| 2-methyl-4-phenylbutyric acid | 2-methyl-4-(p-chloromethylphenyl)butyric acid |

TABLE 1-continued

| Acid | Chloromethyl derivative |
| --- | --- |
| 2-hydroxy-4-phenylbutyric acid | 2-hydroxy-4-(p-chloromethylphenyl)butyric acid |
| phenoxyacetic acid | p-chloromethylphenoxyacetic acid |
| 2-phenoxypropionic acid | 2-(p-chloromethylphenoxy)propionic acid |
| 4-phenoxybutyric acid | 4-(p-chloromethylphenoxy)butyric acid |
| 2-methyl-4-phenoxybutyric acid | 2-methyl-4-(p-chloromethylphenoxy)butyric acid |
| 3-phenoxypropionic acid | 3-(p-chloromethylphenoxy)propionic acid |
| 3-phenoxylactic acid | 3-(p-chloromethylphenoxy)lactic acid |
| anilinoacetic acid | p-chloromethylanilinoacetic acid |
| 2-hydroxy-2-(2-thienyl)acetic acid | 2-hydroxy-2-[2-(5-chloromethyl)thienyl]acetic acid |
| 2-anilinopropionic | 2-(p-chloromethyl)anilinopropionic acid |
| 4-anilinobutyric acid | 4-(p-chloromethylanilino)butyric acid |
| 3-anilinobutyric acid | 3-(p-chloromethylanilino)butyric acid |
| phenylthioacetic acid | p-chloromethylphenylthioacetic acid |
| 2-phenylthiopropionic acid | 2-(p-chloromethylphenyl)thiopropionic acid |
| 4-phenylthiobutyric acid | 4-(p-chloromethylphenyl)thiobutyric acid |
| o-chlorophenylacetic acid | o-chloro-p-chloromethylphenylacetic acid |

EXAMPLE 2 p-Chloromethylphenylglycine hydrochloride

A mixture of 2.03 g of trifluoroacetylated phenylglycine, 0.8 g of zinc chloride in chloromethylether is heated at 65° C for 12 hours. The excess reagent is removed under vacuum, and the residue is dissolved in $CH_2Cl_2$, washed with saturated $NaHCO_3$ solution then saturated sodium chloride solution. The neutral organic phase is dried over $Na_2SO_4$ and concentrated to an oil which was purified by column chromatography. Similarly the chloromethyl derivatives listed in Table II may be prepared from the listed acid.

TABLE II

| Acid | Chloromethyl derivative |
| --- | --- |
| phenylalanine | p-(chloromethylphenyl)alanine HCl |
| 2-amino-4-phenylbutyric acid | 2-amino-4-(p-chloromethylphenyl)butyric acid HCl |
| 2-amino-4-phenoxybutyric acid | 2-amino-4-(p-chloromethylphenoxy)butyric acid HCl |
| 3-phenoxyalanine | 3-(p-chloromethylphenoxy)alanine HCl |
| 2-amino-4-anilinobutyric acid | 2-amino-4-(p-chloromethylanilino)butyric acid HCl |
| 2-amino-4-phenylthiobutyric acid | 2-amino-4-(p-chloromethylphenyl)thiobutyric acid HCl |
| 3-phenylthioalanine | 3-(p-chloromethylphenyl)thioalanine HCl |
| 2-(2-thienyl)glycine | 2-[2-(5-chloromethyl)thienyl]glycine HCl |
| 2-amino-3-(2-thienyl)propionic acid | 2-amino-3-[2-(5-chloromethyl)thienyl]propionic acid HCl |
| 2-amino-4-(2-thienyl)butyric acid | 2-amino-4-[2-(5-chloromethyl)thienyl]butyric acid HCl |

EXAMPLE 3 p-Chloromethylphenylmalonic acid

When in the procedure of Example 1 (A) an equivalent amount of phenylmalonic acid diethyl ester is substituted for phenylacetic acid, p-chloromethylphenylmalonic acid diethyl ester is obtained which yields the corresponding acid upon acid hydrolysis. In a similar manner the chloromethyl derivatives listed in Table III may be prepared when the diethyl ester of the corresponding acid listed in Table III is substituted for phenylmalonic acid diethyl ester.

TABLE III

| Acid | Chloromethyl derivative |
|---|---|
| 2-sulfophenylacetic acid | 2-sulfo-p-chloromethyl-phenylacetic acid |
| 3-phenyl-2-sulfopropionic acid | 3-(p-chloromethyl-phenyl)-2-sulfopropionic acid |
| 4-phenyl-2-sulfobutyric acid | 4-(p-chloromethyl-phenyl)-2-sulfobutyric acid |
| benzylmalonic acid | p-chloromethylbenzylmalonic acid |
| phenethylmalonic acid | p-chloromethylphenethylmalonic acid |
| 2-phenoxyethyl-malonic acid | 2-(p-chloromethyl-phenoxy)ethylmalonic acid |
| 2-phenylthioethyl-malonic acid | 2-(p-chloromethyl-phenyl)thioethyl-malonic acid |
| anilinomethyl-malonic acid | p-chloromethylanilino-methylmalonic acid |
| 2-thienylmalonic acid | 2-[2-(5-chloromethyl)-thienyl]malonic acid |
| 2-thenylmalonic acid | 2-[2-(5-chloromethyl)-thenyl]malonic acid |

EXAMPLE 4

5-Chloromethyl-2-thienylacetyl chloride

2-Thiophenecarboxylic acid is treated in a solution of chloroform with chloromethyl ether in the presence of 0.9 to 2.2 equivalents of aluminum chloride to give 5-chloromethyl-2-thienylcarboxylic acid. Treatment of the obtained acid with excess thionyl chloride at room temperature for about 16 hours yields the acid chloride which is reacted with diazomethane to give the corresponding diazoketone. A methanol solution of the diazoketone is irradiated under nitrogen for about one hour with a high pressure mercury lamp using a Quarz filter. The methyl 5-chloromethyl-2-thienylacetate is obtained upon work up and column chromatography on silica gel. The acetate is hydrolyzed by treatment of a 1:1 mixture of acetic acid and concentrated hydrochloric acid at room temperature overnight to give 5-chloromethyl-2-thienylacetic acid.

When in the procedure of Example 1 (B) 5-chloromethyl-2-thienylacetic acid, is substituted for p-chloromethylphenyl acetic acid, 5-chloromethyl-2-thienylacetyl chloride is obtained.

EXAMPLE 5 o-Hydroxymethylphenylacetic acid lactone

The neutral by-product obtained in Example 1 is purified by sublimation under vacuum (0.05 mm Hg at 80° C) to give o-hydroxymethylphenylacetic acid lactone. M.P. 82° C.

EXAMPLE 6 o-Bromomethylphenylacetyl chloride

To a solution of 5 ml of glacial acetic acid saturated with hydrogen bromide gas is added at 0° C a solution of o-hydroxymethylphenylacetic acid lactone (0.55 g) in 2 ml of glacial acetic acid. The mixture is stirred at room temperature for two hours then refluxed for one hour during which time hydrogen bromide gas is bubbled into the mixture. The excess lactone and solvent are removed under high vacuum at room temperature. The resulting oily residue is triturated three times with hexane to give o-bromomethylphenylacetic acid. M.P. 110° C.

A solution of 0.18 g of o-bromomethylphenylacetic acid in excess thionyl chloride is stirred at room temperature for 18 hours after which the unreacted thionyl chloride is removed under high vacuum to give o-bromomethylphenylacetyl chloride as an oily residue.

EXAMPLE 7 o-Chloromethyl-p-methoxymandelic acid chloride

A solution of 1.1 g of 2-chloromethyl-4-methoxy-mandelic acid, obtained by the procedure described by B. Reichert et al., Pharmazie 5, 10 (1950), in 25 ml of thionyl chloride is stirred at room temperature for about 16 hours after which the excess thionyl chloride is removed under high vacuum to give o-chloromethyl-p-methoxymandelic acid chloride as an oil.

EXAMPLE 8

3-[(Acetyloxy)methyl]-7-amino-8-oxo-5-thia-1-azabicyclo-[4.2.0]oct-2-ene-2-carboxylic acid propionyloxymethyl ester To 35 ml of dimethyl formamide is added 7.5 g of the sodium salt of 3-[(acetyloxy)methyl]-7-amino-8-oxo-5-thia-1-azabicyclo[4.2.0]oct-2-ene-2-carboxylic acid, and the solution is stirred at room temperature for about 30 minutes after which 8 ml of chloromethylpropionate is added. Stirring is continued at room temperature for about 3 hours. The mixture is diluted with ethyl acetate and washed with water. The organic layer is separated and evaporated to dryness. The residue is recrystallized from ethyl acetate to give 3-[(acetyloxy)-methyl]-7-amino-8-oxo-5-thia-1-azabicyclo[4.2.0]oct-2-ene-2-carboxylic acid propionyloxymethyl ester.

In a similar manner when an appropriate amount of chloromethylpivalate, chloromethylacetate or chloromethylbutyrate is substituted for chloromethylpropionate, the following respective products are obtained: 3-[(acetyloxy)methyl]-7-amino-8-oxo-5-thia-1-azabicyclo-[4.2.0]oct-2-ene-2-carboxylic acid pivalyloxymethyl ester, 3-[(acetyloxy)methyl]-7-amino-8-oxo-5-thia-1-azabicyclo-[4.2.0]oct-2-ene-2-carboxylic acid acetyloxymethyl ester, 3-[(acetyloxy)methyl]-7-amino-8-oxo-5-thia-1-azabicyclo[4.2.0]oct-2-ene-2-carboxylic acid butyryloxymethyl ester.

EXAMPLE 9

3-[(Acetyloxy)methyl]-7-amino-8-oxo-5-thia-1-azabicyclo[4.2.0]oct-2-ene-2-carboxylic acid 2-amino-3-methylbutyryloxymethyl ester A suspension of 5 grams of 3-[(acetyloxy)methyl]-7-amino-8-oxo-5-thia-1-azabicyclo[4.2.0]oct-2-ene-2-carboxylic acid sodium salt and 8.5 grams of N-tert-butoxycarbonyl-L-valine chloromethyl ester, which is prepared by the general procedure described in W. German Offen. 2,236,620, are mixed in 100 ml of dimethyl formamide and stirred for 72 hours. The mixture is diluted with ethyl acetate, washed with water with aqueous bicarbonate and again with water. The organic layer is dried over magnesium sulfate, filtered, and evaporated to dryness to give 3-[(acetyloxy)-methyl]-7-amino-8-oxo-5-thia-1-azabicyclo[4.2.0oct-2-ene-2-carboxylic acid N-tert-butoxycarbonyl-2-amino-3-methylbutryryloxymethyl ester from which the amine protecting group is removed by standard procedures to give the title product.

EXAMPLE 10

3 - [(Acetyloxy)methyl] - 7 - amino - 8 - oxo - 5 - thia - 1 - azabicyclo - [4.2.0]oct - 2 - ene - 2 - carboxylic acid N - ethoxycarbonyl - N - methylaminomethyl ester 725 Mg (2.5 mM) of the sodium salt of 3 - [(acetyloxy)-methyl]-7-amino-8-oxo-5-thia-1-azabicyclo[4.2.0]oct-2-ene-2-carboxylic acid in 50 ml of dimethyl formamide is treated at room temperature with 375 mg (2.5 mM) of N - chloromethyl - N - methylurethane for one hour. The mixture is carefully poured into ice water and the precipitated solid is removed by filtration and washed with water. The solid is dissolved in ethylacetate and washed with aqueous sodium bicarbonate and then with water. The organic layer is dried over magnesium sulfate, filtered and evaporated to dryness in vacuo to give 3 - [(acetyloxy)methyl] - 7 - amino - 8 - oxo - 5 - thia - 1 - azabicyclo[4.2.0]oct - 2 - ene - 2 - carboxylic acid N - ethoxycarbonyl - N - methylaminomethyl ester.

When in the above procedure an appropriate amount of N-methyl-N-propionylaminomethyl chloride, N:butyrylaminomethyl chloride, N-acetylaminomethyl chloride, or N-methylN-ethoxycarbonylaminomethyl chloride is substituted for N-chloromethyl-N-methylurethane the following respective compounds are obtained:

3-[(acetyloxy)methyl]-7-amino-8-oxo-5-thia-1-azabicyclo-[4.2.0]oct-2-ene-2-carboxylic acid N-methyl-N-propionylaminomethyl ester, 3-[(acetyloxy)methyl]-7-amino-8-oxo-5-thia-1-azabicyclo-[4.2.0]oct-2-ene-2-carboxylic acid N-butyrylaminomethyl ester, 3-[(acetyloxy)methyl]-7-amino-8-oxo-5-thia-1-azabicyclo-[4.2.0]oct-2-ene-2-carboxylic acid N-acetylaminomethyl ester and, 3-[(acetyloxy)methyl]-7-amino-8-oxo-5-thia-1-azabicyclo-[4.2.0]oct-2-ene-2-carboxylic acid N-methyl-N-ethoxycarbonylaminomethyl ester.

EXAMPLE 11

3-[(Acetyloxy)methyl]-7-amino-8-oxo-5-thia-1-azabicyclo-[4.2.0]oct-2-ene-2-carboxylic acid p-pivalyloxybenzyl ester To a suspension of 6.6 mM of 3-[(acetyloxy)methyl]-7-amino-8-oxo-5-thia-1-azabicyclo[4.2.0]oct-2-ene-2-carboxylic acid sodium salt in 35 ml of dimethyl formamide (DMF) is added 2 equivalents of ppivalyloxybenzyl alcohol followed by cooling to 0° C after which 7.2 mM of dicyclohexylcarbodiimide in 7.5 ml of DMF is added dropwise with stirring. The mixture is stirred at 0° C for one hour and an additional four hours at room temperature. The formed dicyclohexylurea is removed by filtration. The filtrate is diluted with chloroform, washed with water, dried over magnesium sulfate, filtered, and evaporated in vacuo to give 3-[(acetyloxy)-methyl]-7-amino-8-oxo-5-thia-1-azabicyclo[4.2.0]oct-2-ene-2-carboxylic acid p-pivalyloxybenzyl ester.

When in the above procedure an appropriate amount of p-(propionyloxy)benzyl alcohol, p-(acetyloxy)benzyl alcohol, or p-(valeryloxy)benzyl alcohol is substituted for p-pivalyloxybenzyl alcohol the following respective products are obtained:

3-[(acetyloxy)methyl]-7-amino-8-oxo-5-thia-1-azabicyclo-[4.2.0]oct-2-ene-2-carboxylic acid p-(propionyloxy)benzyl ester, 3-[(acetyloxy)methyl]-7-amino-8-oxo-5-thia-1-azabicyclo-[4.2.0]oct-2-ene-2-carboxylic acid p-(acetyloxy)benzyl ester, and 3-[(acetyloxy)methyl]-7-amino-8-oxo-5-thia-1-azabicyclo-[4.2.0]oct-2-ene-2-carboxylic acid p-(valeryloxy)benzyl ester.

EXAMPLE 12

3-(2-Methyl-1,3,4-thiadiazol-5-ylthio)-7-amino-8-oxo-5-thia-1-azabicyclo[4.2.0]oct-2-ene-2-carboxylic acid In about 1 liter of water is dissolved 0.1 mole of the sodium salt of 3-[(acetyloxy)methyl]-7-amino-8-oxo-5-thia-1-azabicyclo[4.2.0]oct-2-ene-2-carboxylic acid at 70° C under nitrogen atmosphere. To the solution is added 1 equivalent of sodium bicarbonate and 2 equivalents of 2-methyl-1,3,4-thiadiazol-5-ylthiol. The mixture is stirred at 70° C for 3 hours after which the pH is adjusted to 3.5, and the resulting precipitate collected giving 3-(2-methyl-1,3,4-thiadiazol-5-ylthio)-7-amino-8-oxo-5-thia-1-azabicyclo[4.2.0]oct-2-ene-2-carboxylic acid.

When in the above procedure an equivalent amount of 1,3,4-thiadiazol-5-ylthiol, 3-methyl-1,2,4-thiadiazol-5-ylthiol, tetrazol-5-ylthiol, 1-methyltetrazol-5-ylthiol or 2-methyl-1,3,4-oxadiazol-5ylthiol is substituted for 2-methyl-1,3,4-thiadiazol-5-ylthiol the following respective products are obtained:

3-(1,3,4-thiadiazol-5-ylthio)-7-amino-8-oxo-5-thia-1-azabicyclo[4.2.0]oct-2-ene-2-carboxylic acid, 3-(3-methyl-1,2,4-thiadiazol-5-ylthio)-7-amino-8-oxo-5-thia-1-azabicyclo[4.2.0]oct-2-ene-2-carboxylic acid, 3-(tetrazol-5-ylthio)-7-amino-8-oxo-5thia-1-azabicyclo-[4.2.0]oct-2-ene-2-carboxylic acid, 3-(1-methyltetrazol-5-ylthio)-7-amino-8-oxo-5thia-1-azabicyclo[4.2.0]oct-2-ene-2-carboxylic acid, and 3-(2-methyl-1,3,4-oxadiazol-5-ylthio)-7-amino-8-oxo-5-thia-1-azabicyclo[4.2.0]oct-2-ene-2-carboxylic acid.

EXAMPLE 13

When in the procedure of Example 12 appropriate amounts of the sodium salt of the cephalosporin derivative and the heterocyclicthiol derivative listed below in Table IV are substituted respectively for the sodium salt of 3-[(acetyloxy)methyl-]-7-amino-8-oxo-5-thia-1-azabicyclo-[4.2.0]oct-2-ene-2-carboxylic acid and 2-methyl-1,3,4-thiadiazol-5-ylthiol the respective products listed in Table IV are obtained.

TABLE IV

| Cephalosporin Derivative | Heterocyclicthiol | Product |
| --- | --- | --- |
| 3-[(acetyloxy)methyl]-7-amino-8-oxo-5-thia-1-azabicyclo[4.2.0]oct-2-ene-2-carboxylic acid propionyloxymethyl ester | 3-methyl-1,2,4-thiadiazol-5-ylthiol | 3-(3-methyl-1,2,4-thiadiazol-5-ylthio)-7-amino-8-oxo-5-thia-1-azabicyclo[4.2.0]oct-2-ene-2-carboxylic acid propionyloxymethyl ester |
| 3-[(acetyloxy)methyl]-7-amino-8-oxo-5-thia-1-azabicyclo[4.2.0]oct-2-ene-2-carboxylic acid p-pivalyloxymethyl ester | 1-methyltetrazol-5-ylthiol | 3-(1-methyltetrazol-5-ylthio)-7-amino-8-oxo-5-thia-1-azabicyclo-[4.2.0]oct-2-ene-2-carboxylic acid pivalyloxymethyl ester |
| 3-[(acetyloxy)methyl]-7-amino-8-oxo-5-thia-1-azabicyclo[4.2.0]oct-2-ene-2-carboxylic acid acetyloxymethyl ester | 1,3,4-thiadiazol-5-ylthiol | 3-(1,3,4-thiadiazol-5-ylthio)-7-amino-8-oxo-5-thia-1-azabicyclo-[4.2.0]oct-2-ene-2-carboxylic acid acetyloxymethyl ester |
| 3-[(acetyloxy)methyl]-7-amino-8-oxo-5-thia-1-azabicyclo[4.2.0]oct-2-ene-2-carboxylic acid butyryloxymethyl ester | tetrazol-5-ylthiol | 3-(tetrazol-5-ylthio)-7-amino-8-oxo-5-thia-1-azabicyclo[4.2.0]oct-2-ene-2-carboxylic acid butyryloxymethyl ester |
| 3-[(acetyloxy)methyl]-7-amino-8-oxo-5-thia-1-azabicyclo[4.2.0]oct-2-ene-2-carboxylic acid 2-amino-3-methylbutyryloxymethyl ester | 2-methyl-1,3,4-oxadiazol-5-ylthiol | 3-(2-methyl-1,3,4-oxadiazol-5-ylthio)-7-amino-8-oxo-5-thia-1-azabicyclo[4.2.0]oct-2-ene-2-carboxylic acid 2-amino-3-methylbutyryloxymethyl ester |
| 3-[(acetyloxy)methyl]-7-amino-8-oxo-5-thia-1-azabicyclo[4.2.0]oct-2-ene-2-carboxylic acid N-ethoxycarbonyl-N-methylaminomethyl ester | 2-methyl-1,3,4-thiadiazol-5-ylthiol | 3-(2-methyl-1,3,4-thiadiazol-5-ylthio)-7-amino-8-oxo-5-thia-1-azabicyclo[4.2.0]oct-2-ene-2-carboxylic acid N-ethoxycarbonyl-N-methylaminomethyl ester |
| 3-[(acetyloxy)methyl]-7-amino-8-oxo-5-thia-1-azabicyclo[4.2.0]oct-2-ene-2-carboxylic acid p-pivalyloxybenzyl ester | 1-methyltetrazol-5-ylthiol | 3-(1-methyltetrazol-5-ylthio)-7-amino-8-oxo-5-thia-1-azabicyclo-[4.2.0]oct-2-ene-2-carboxylic acid p-pivalyloxybenzyl ester |
| 3-[(acetyloxy)methyl]-7-amino-7-methoxy-8-oxo-5-thia-1-azabicyclo-[4.2.0]oct-2-ene-2-carboxylic acid (prepared by acid hydrolysis of the corresponding benzhydryl ester described in U.S. patent 3,778,432) | 2-methyl-1,3,4-thiadiazol-5-ylthiol | 3-(2-methyl-1,3,4-thiadiazol-5-ylthio)-7-amino-7-methoxy-8-oxo-5-thia-1-azabicyclo[4.2.0]oct-2-ene-2-carboxylic acid |
| 3-[(acetyloxy)methyl]-7-amino-8-oxo-5-thia-1-azabicyclo[4.2.0]oct-2-ene-2-carboxylic acid p-(propionyloxy)-benzyl ester | 1-methyltetrazol-5-ylthiol | 3-(1-methyltetrazol-5-ylthio)-7-amino-8-oxo-5-thia-1-azabicyclo-[4.2.0]oct-2-ene-2-carboxylic acid p-(propionyloxy)benzyl ester |
| 3-[(acetyloxy)methyl]-7-amino-8-oxo-5-thia-1-azabicyclo[4.2.0]oct-2-ene-2-carboxylic acid p-(acetyloxy)benzyl ester | tetrazol-5-ylthiol | 3-(tetrazol-5-ylthio)-7-amino-8-oxo-5-thia-1-azabicyclo[4.2.0]-oct-2-ene-2-carboxylic acid p-(acetyloxy)benzyl ester |
| 3-[(acetyloxy)methyl]-7-amino-8-oxo-5-thia-1-azabicyclo[4.2.0]oct-2-ene-2-carboxylic acid p-(valeryloxy)benzyl ester | 3-methyl-1,2,4-thiadiazol-5-ylthiol | 3-(3-methyl-1,2,4-thiadiazol-5-ylthio)-7-amino-8-oxo-5-thia-1-azabicyclo[4.2.0]oct-2-ene-2-carboxylic acid p-(valeryloxy)benzyl ester |

EXAMPLE 14

3-[Acetyloxy)methyl]-7-[[2-[4-(chloromethyl)-phenyl]-acetyl]amino]-8-oxo-5-thia-1-azabicyclo[4.2.0]oct-2-ene-2-carboxylic acid A mixture of 1 g of 3-[(acetyloxy)methyl]-7-amino-8-oxo-5-thia-1-azabicyclo[4.2.0]oct-2-ene-2-carboxylic acid and 1 g of p-chloromethylphenylacetyl chloride in 45 ml of ethyl acetate is refluxed for about 2 hours after which the solvent is removed under vacuum yielding a yellow-brown amorphous product which is chromatographed on silica gel using benzene-acetone as the eluant to give 3-[(acetyloxy)methyl]-7-[[2-[4-(chloromethyl)phenyl]acetyl]amino]-8-oxo-5-thia-1-azabicyclo[4.2.0]oct-2-ene-2-carboxylic acid. M.P. 164°–165° C. (dec.).

In a similar manner when an appropriate amount of each of the acetyloxymethyl ester, the propionyloxybenzyl ester, the 2-amino-3-methylbutyryloxymethyl ester, the pivalyloxymethyl ester, and the N-ethoxycarbonyl-N-methylaminomethyl ester of 3-[(acetyloxy)methyl]-7-amino-8-oxo-5-thia-1-azabicyclo[4.2.0]oct-2-ene-2-carboxylic acid or 3-(1-methyltetrazol-5-ylthio)-7-amino-8-oxo-5-thia-1-azabicyclo[4.2.0]oct-2-ene-2-carboxylic acid pivalyloxybenzylester, 3-(2-methyl-1,3,4-thiadiazol-5-ylthio)-7-amino-8-oxo-5-thia-1-azabicyclo[4.2.0]oct-2-ene-2-carboxylic acid propionyloxymethyl ester or the corresponding pivalyloxymethyl ester or 3-(2-methyl-1,3,4-thiadiazol-5-ylthio)-7-amino-8-oxo-5-thia-1-azabicyclo[4.2.0]oct-2-ene-2-carboxylic acid, or 3-(1-methyltetrazol-5-ylthio)-7-amino-8-oxo-5-thia-1-azabicyclo[4.2.0]oct-2-ene-2-carboxylic acid is substituted for the free 7-aminocephalosporanic acid in the above Example, the following compounds are obtained:

3-[(acetyloxy)methyl]-7-[[2-[4-(chloromethyl)-phenyl]-acetyl]amino]-8-oxo-5-thia-1-azabicyclo[4.2.0]oct-2-ene-2-carboxylic acid acetyloxymethyl ester, 3-[(acetyloxy)methyl]-7-[[2-[4-(chloromethyl)-phenyl]-acetyl]amino]-8-oxo-5-thia-1-azabicyclo[4.2.0]oct-2-ene-2-carboxylic acid propionyloxybenzyl ester, 3-[(acetyloxy)methyl]-7-[[2-[4-(chloromethyl)-phenyl]-acetyl]amino]-8-oxo-5-thia-1-azabicyclo[4.2.0]oct-2-ene-2-carboxylic acid 2-amino-3-methylbutyryloxymethyl ester, 3-[(acetyloxy)methyl]-7-[[2-[4-(chloromethyl)-phenyl]-acetyl]amino]-8-oxo-5-thia-1-azabicyclo[4.2.0]oct-2-ene-2-carboxylic acid pivalyloxymethyl ester, 3-[(acetyloxy)methyl]-7-[[2-[4-(chloromethyl)-phenyl]-acetyl]amino]-8-oxo-5-thia-1-azabicyclo[4.2.0]oct-2-ene-2-carboxylic acid N-ethoxycarbonyl-N-methylaminomethyl ester, 3-(1-methyltetrazol-5-ylthio)-7-[[2-[4-(chloromethyl)phenyl]-acetyl]amino]-8-oxo-5-thia-1-azabicyclo[4.2.0]oct-2-ene-2-carboxylic acid pivalyloxybenzyl ester, 3-(2-methyl-1,3,4-thiadiazol-5-ylthio)-7-[[2-[4-(chloromethyl)phenyl]acetyl]amino]-8-oxo-5-thia-1-azabicyclo-[4.2.0]oct-2-ene-2-carboxylic acid propionyloxymethyl ester, 3-(2-methyl-1,3,4-thiadiazol-5-ylthio)-7-[[2-[4-(chloromethyl)phenyl]acetyl]amino]-8-oxo-5-thia-1-azabicyclo-[4.2.0]oct-2-ene-2-carboxylic acid pivalyloxymethyl ester, 3-(2-methyl-1,3,4-thiadiazol-5-ylthio)-7-[[2-[4-(chloromethyl)phenyl]acetyl]amino]-8-oxo-5-thia-1-azabicyclo-[4.2.0]oct-2-ene-2-carboxylic acid, and 3-(1-methyltetrazol-5-ylthio)-7-[[2-[4-(chloromethyl)-phenyl]acetyl]amino]-8-oxo-5-thia-1azabicyclo[4.2.0]-oct-2-ene-2-carboxylic acid.

EXAMPLE 15

7-[[2-[4-(Chloromethyl)phenyl]acetyl]amino]-3-methyl-8-oxo-5-thia-1-azabicyclo[4.2.0]oct-2-ene-2carboxylic acid By the procedure of Example 14, only substituting 1 g of 7-amino-3-methyl-8-oxo-5-thia-1-azabicyclo[4.2.-0]oct-2-ene-2-carboxylic acid for 3-acetyloxymethyl-7-amino-8-oxo-5-thia-1-azabicyclo[4.2.0]oct-2-ene-2-carboxylic acid, 7-[[2-[4-(chloromethyl)phenyl]acetyl]amino]-3-methyl-8-oxo-5-thia-1-azabicyclo[4.2.0]oct-2-ene-2-carboxylic acid is obtained. M.P. 145°–146° C.

EXAMPLE 16

6-[[2-[4-(Chloromethyl)phenyl]acetyl]amino]-3,3-dimethyl-7-oxo-4-thia-1-azabicyclo[3.2.0]heptane-2-carboxylic acid When in Example 14 an appropriate amount of the triethylamine salt of 6-amino-3,3-dimethyl-7-oxo-4-thia-1-azabicyclo[3.2.0]heptane-2-carboxylic acid is substituted for 3-[(acetyloxy)methyl]-7-amino-8-oxo-5-thia-1-azabicyclo[4.2.0]-oct-2-ene-2-carboxylic acid, 6-[[2-[4-(chloromethyl)phenyl]-acetyl]amino]-3,3-dimethyl-7-oxo-4-thia-1-azabicyclo[3.2.0]heptane-2-carboxylic acid is obtained.

EXAMPLE 17

3-[(Acetyloxy)methyl]-7-[[2-[4-(chloromethyl)-phenyl]-2-aminoacetyl]amino]-8-oxo-5-thia-1-azabicyclo[4.2.0]oct-2-ene-2-carboxylic acid p-Chloromethylphenylglycine wherein the amino group is protected with tert-butoxycarbonyl, is treated with isobutyl chloroformate in the presence of triethylamine. The thus obtained mixed anhydride is reacted with the triethylamine salt of 3-[(acetyloxy)methyl]-7-amino-8-oxo-5-thio-1-azabicyclo[4.2.0]oct-2-ene-2-carboxylic acid at 0° C for about 4 hours. The resulting product is isolated, and the amine protecting group is removed by acid hydrolysis to give, 3-[(acetyloxy)methyl]-7-[[2-[4-(chloromethyl)phenyl]-2-aminoacetyl]amino]-8-oxo-5-thia-1-azabicyclo-[4.2.0]oct-2-ene-2-carboxylic acid.

When in the above procedure an appropriate amount of the triethylamine salt of 3-(2-methyl-1,3,4-thiadiazol-5-ylthio)-7-amino-8-oxo-5-thia-1-azabicyclo[4.2.0]oct-2-ene-2-carboxylic acid or 3-(1-methyltetrazol-5-ylthio)-7-amino-8-oxo-5-thia-1-azabicyclo[4.2.0]oct-2-ene-2-carboxylic acid, 3-[(acetyloxy)methyl]-7-amino-8-oxo-5-thia-1-azabicyclo[4.2.0]oct-2-ene-2-carboxylic acid pivalyloxymethyl ester is substituted for the triethylamine salt of 3-[(acetyloxy)methyl]-7-amino-8-oxo-5-thia-1-azabicyclo[4.2.0]-oct-2-ene-2-carboxylic acid the following respective products are obtained:

3-(2-methyl-1,3,4-thiadiazol-5-ylthio)-7-[[2-[4-(chloromethyl)phenyl]-2-aminoacetyl]amino]-8-oxo-5-thia-1-azabicyclo[4.2.0]oct-2-ene-2-carboxylic acid, 3-(1-methyltetrazol-5-ylthio)-7-[[2-[4-(chloromethyl)-phenyl]-2-aminoacetyl]amino]-8-oxo-5-thia-1-azabicyclo-[4.2.0]oct-2-ene-2-carboxylic acid, 3-[(acetyloxy)methyl]-7-[[2-[4-(chloromethyl)-phenyl]-2-aminoacetyl]amino]-8-oxo-5-thia-1-azabicyclo[4.2.0]oct-2-ene-2-carboxylic acid pivalyloxymethyl ester.

EXAMPLE 18

6-[[2-[4-(Chloromethyl)phenyl]-2-aminoacetyl]amino]-3,3-dimethyl-7-oxo-4-thia-1-azabicyclo[3.2.0]heptane-2-carboxylic acid When in the procedure of Example 17 an appropriate amount of the triethylamine salt of 6-amino-3,3-dimethyl-7-oxo-4-thia-1-azabicyclo[3.2.0]heptane-2-carboxylic acid is substituted for the triethylamine salt of 3-[(acetyloxy)-methyl]-7-amino-8-oxo-5-thia-1-azabicyclo[4.2.0]oct-2-ene-2-carboxylic acid, 6-[[2-[4-(chloromethyl)phenyl]-2-aminoacetyl]amino]-3,3-dimethyl-7-oxo-4-thia-1-azabicyclo[3.2.0]heptane-2-carboxylic acid is obtained.

EXAMPLE 19

3-[(Acetyloxy)methyl]-7-[[2-[2-(chloromethyl)-4-methoxyphenyl]-2-hydroxyacetyl]amino]-8-oxo-5-thia-1-azabicyclo-[4.2.0]oct-2-ene-2-carboxylic acid A mixture of 1 g of 3-[(acetyloxy)methyl]-7-amino-8-oxo-5-thia-1-azabicyclo[4.2.0]oct-2-ene-2-carboxylic acid and 1.2 g of 2-chloromethyl-4-methoxymandelic acid chloride in 200 ml of ethyl acetate is refluxed for 50 minutes after which the solvent is removed under high vacuum. The resulting product is chromatographed on silica gel using benzene-acetone as the eluant. The product obtained is triturated with ether to give 3-[(acetyloxy)methyl]-7-[[2-[2-(chloromethyl)-4-methoxyphenyl]-2-hydroxyacetyl]amino]-8-oxo-5-thia-1-azabicyclo[4.2.0]oct-2-ene-2-carboxylic acid. M.P. 140°–142° C (dec.).

When in the above procedure an appropriate amount of 3-(2-methyl-1,3,4-thiadiazol-5-ylthio)-7-amino-8-oxo-5-thia-1-azabicyclo[4.2.0]oct-2-ene-2-carboxylic acid or 3-(1-methyltetrazol-5-ylthio)-7-amino-8-oxo-5-thia-1-azabicyclo[4.2.0]oct-2-ene-2-carboxylic acid is substituted for the corresponding 3-[(acetoxy)methyl] derivative and 2-(p-chloromethylphenyl)mandelic acid chloride is substituted for 2-chloromethyl-4-methoxymandelic acid, 3-(2-methyl-1,3,4-thiadiazol-5-ylthio]-7-[[2-[4-(chloromethyl)-phenyl]-2-hydroxyacetyl]amino]-8-oxo-5-thia-1-azabicyclo-[4.2.0]oct-2-ene-2-carboxylic acid and 3-(1-methyltetrazol-5-ylthio)-7-[[2-[4-(chloromethyl)phenyl]-2-hydroxyacetyl]-amino]-8-oxo-5-thia-1-azabicyclo[4.2.0]oct-2-ene-2-carboxylic acid are obtained.

EXAMPLE 20

6-[[2-[2-(Chloromethyl)-4-methoxyphenyl]-2-hydroxyacetyl]-amino]-3,3-dimethyl-7-oxo-4-thia-1-azabicyclo[3.2.0]-heptane-2-carboxylic acid When in Example 19 an appropriate amount of the triethylamine salt of 6-amino-3,3-dimethyl-7-oxo-4-thia-1-azabicyclo[3.2.0]heptane-2-carboxylic acid is substituted for 3-[(acetyloxy)methyl]-7-amino-8-oxo-5-thia-1-azabicyclo[4.2.0]-oct-2-ene-2-carboxylic acid, 6-[[2-[2-(chloromethyl)-4-methoxyphenyl]-2-hydroxyacetyl]amino]-3,3-dimethyl-7-oxo-4-thia-1-azabicyclo[3.2.0]heptane-2-carboxylic acid is obtained.

EXAMPLE 21

3-[(Acetyloxy -7-[[2-[5-(chloromethyl)-2-thienyl]acetyl]amino]-8-oxo-5-thia-1-azabicyclo[4.2.0]oct-2-ene-carboxylic acid A mixture of 1.2 equivalents of 5-chloromethyl-2-thienylacetyl chloride and 1 equivalent of 3-[(acetyloxy)-methyl]-7-amino-8-oxo-5-thia-1-azabicyclo[4.2.-0]oct-2-ene-2-carboxylic acid is refluxed for 50 minutes in ethyl acetate after which the solvent is removed and the remaining product is purified by column chromatography on silica gel to give 3-[(acetyloxy)methyl]-7-[[2-[5-(chloromethyl)-2-thienyl]acetyl]amino]-8-oxo-5-thia-1-azabicyclo[4.2.0]oct-2-ene-2-carboxylic acid.

EXAMPLE 22

3-[(Acetyloxy)methyl]-7-[[2-[4-(chloromethyl)-phenyl]-2-carboxyacetyl]amino]-8-oxo-5-thia-1-azabicyclo[4.2.0]-oct-2-ene-2-carboxylic acid α-Carboxy-p-chloromethylphenylacetyl nitrophenyl polymer, prepared according to the procedure described in Canadian Patent No. 892,580, carrying 4 m. mole of p-chloromethylphenylmalonic acid is suspended for about 8 hours in 20 ml of dry methylene chloride solution containing 1 m. mole of 3-[(acetyloxy)methyl]-7-amino-8-oxo-5-thia-1-azabicyclo[4.2.-0]oct-2-ene-2-carboxylic acid triethylammonium salt, which is prepared from 544 mg of 7-aminocephalosporanic acid (1 m. mole) and 0.56 ml of triethylamine (1 m. mole) at room temperature. After only traces of 7-aminocephalosporanic acid remain in solution, which is determined by thin layer chromatography on cellulose in 70% aqueous propanol, the polymer is filtered off and washed with 3 portions of 50 ml each of methylene chloride. The combined filtrates are evaporated and the residue is dissolved in 20 ml or distilled water. This solution is acidified to pH 2 by adding 0.2N hydrochloric acid and extracted twice with ethyl acetate. The organic solution is dried over sodium sulfate and evaporated at room temperature. The remaining solid is dried overnight over phosphorus pentoxide under vacuum to give 3-[(acetyloxy)-methyl]-7-[[2-[4-(chloromethyl)phenyl]-2-carboxyacetyl]-amino]-8-oxo-5-thia-1-azabicyclo[4.2.0]oct-2-ene-2-carboxylic acid.

When in the above procedure an appropriate amount of 3-(2-methyl-1,3,4-thiadiazol-5-ylthio)-7-amino-8-oxo-5-thia-1-azabicyclo[4.2.0]oct-2-ene-2-carboxylic acid, 3-[(acetyloxy)methyl]-7-amino-8-oxo-5-thia-1-azabicyclo[4.2.0]oct-2-ene-2-carboxylic acid pivalyloxymethyl ester, or 3-(1-methyltetrazol-5-ylthio)-7-amino-8-oxo-5-thia-1-azabicyclo[4.2.0]oct-2-ene-2-carboxylic acid pivalyloxybenzyl ester is substituted for 3-[(acetyloxy)methyl]-7-amino-8-oxo-5-thia-1-azabicyclo[4.2.0]oct-2-ene-2-carboxylic acid the following products are obtained:

3-(2-methyl-1,3,4-thiadiazol-5-ylthio)-7-[[2-[4-(chloromethyl)phenyl]-2-carboxyacetyl]amino]-8-oxo-5-thia-1-azabicyclo[4.2.0]oct-2-ene-2-carboxylic acid, 3-[(acetyloxy)methyl]-7-[[2-[4-(chloromethyl phenyl]-2-carboxyacetyl]amino]-8-oxo-5-thia-1-azabicyclo[4.2.0]-oct-2-ene-2-carboxylic acid pivalyloxymethyl ester, and 3-(1-methyltetrazol-5-ylthio)-7-[[2-[4-(chloromethyl)phenyl]-2-carboxyacetyl]amino]-8-oxo-5-thia-1-azabicyclo[4.2.0]oct-2-ene-2-carboxylic acid pivalyloxybenzyl ester.

EXAMPLE 23

When in the procedure of Example 14 an appropriate amount of an acid chloride listed in Table V is substituted for p-chloromethylphenylacetyl chloride the respective cephalosporin derivatives listed in Table V are obtained.

TABLE V

| Acid Chloride | Cephalosporin Derivative |
| --- | --- |
| p-chloromethylhydrotropic acid chloride | 3-[(acetyloxy)methyl]-7-[[2-[4-(chloromethyl)-phenyl]-2-methylacetyl]amino]-8-oxo-5-thia-1-azabicyclo[4.2.0]oct-2-ene-2-carboxylic acid |
| p-chloromethyldihydrocinnamic acid chloride | 3-[(acetyloxy)methyl]-7-[[3-[4-(chloromethyl)-phenyl]propionyl]amino]-8-oxo-5-thia-1-azabicyclo[4.2.0]oct-2-ene-2-carboxylic acid |
| p-chloromethyl-2-methylhydrocinnamic acid chloride | 3-[(acetyloxy)methyl]-7-[[3-[4-(chloromethyl)-phenyl]-2-methylpropionyl]amino]-8-oxo-5-thia-1-azabicyclo[4.2.0]oct-2-ene-2-carboxylic acid |
| 2-methyl-4-(p-chloromethylphenyl)butyric-acid chloride | 3-[(acetyloxy)methyl]-7-[[4-[4-(chloromethyl)phenyl]-2-methylbutyryl]amino]-8-oxo-5-thia-1-azabicyclo[4.2.0]oct-2-ene-2-carboxylic acid |
| p-chloromethylphenoxyacetic acid chloride | 3-[(acetyloxy)methyl]-7-[[2-[4-(chloromethyl)-phenoxy]acetyl]amino]-8-oxo-5-thia-1-azabicyclo[4.2.0]oct-2-ene-2-carboxylic acid |
| 2-(p-chloromethylphenoxy)propionic acid chloride | 3-[(acetyloxy)methyl]-7-[[2-[4-(chloromethyl)-phenoxy]2-methylacetyl]amino]-8-oxo-5-thia-1-azabicyclo[4.2.0]oct-2-ene-2-carboxylic acid |
| 2-methyl-4-(p-chloromethylphenoxy)butyric acid chloride | 3-[(acetyloxy)methyl]-7-[[4-[4-(chloromethyl)-phenoxy]-2-methylbutyryl]amino]-8-oxo-5-thia-1-azabicyclo[4.2.0]oct-2-ene-2-carboxylic acid |
| p-chloromethylanilinoacetic acid chloride | 3-[(acetyloxy)methyl]-7-[[2-[4-(chloromethyl)-anilino]acetyl]amino]-8-oxo-5-thia-1-azabicyclo[4.2.0]oct-2-ene-2-carboxylic acid |
| 3-(p-chloromethylanilino)butyric acid chloride | 3-[(acetyloxy)methyl]-7-[[3-[4-(chloromethyl)-anilino]-2-methylpropionyl]amino]-8-oxo-5-thia- |

TABLE V-continued

| Acid Chloride | Cephalosporin Derivative |
| --- | --- |
| p-chloromethylphenylthioacetic acid chloride | 1-azabicyclo[4.2.0]oct-2-ene-2-carboxylic acid 3-[(acetyloxy)methyl]-7-[[2-[4-(chloromethyl)-phenylthio]acetyl]amino]-8-oxo-5-thia-1-azabicyclo[4.2.0]oct-2-ene-2-carboxylic acid |
| o-chloro-p-chloromethylphenylacetic acid chloride | 3-[(acetyloxy)methyl]-7-[[2-[2-(chloro)-4-(chloromethyl)phenyl]acetyl]amino]-8-oxo-5-thia-1-azabicyclo[4.2.0]oct-2-ene-2-carboxylic acid |
| 4-(p-chloromethylphenyl)thiobutyric acid chloride | 3-[(acetyloxy)methyl]-7-[[4-[4-(chloromethyl)-phenylthio]butyryl]amino]-8-oxo-5-thia-1-azabicyclo[4.2.0]oct-2-ene-2-carboxylic acid |

In a similar manner as described in Example 14 when an appropriate amount of the triethylamine salt of 6-amino-3,3-dimethyl-7-oxo-4-thia-1-azabycyclo[3.2.0-]heptane-2-carboxylic acid is reacted with an appropriate amount of the acid chlorides listed in Table V the following respective penicillin derivatives are obtained.

6-[[2-[4-(chloromethyl)phenyl]-2-methylacetyl]amino]-3,3-dimethyl-7-oxo-4-thia-1-azabicyclo[3.2.0]heptane-2-carboxylic acid, 6-[[3-[4-(chloromethyl)phenyl]propionyl]amino]-3,3-dimethyl-7-oxo-4-thia-1-azabicyclo[3.2.0]heptane-2-carboxylic acid, 6-[[3-[4(chloromethyl)phenyl]-2-methylpropionyl]amino]-3,3-dimethyl-7-oxo-4-thia-1-azabicyclo[3.2.0]heptane-2-carboxylic acid, 6-[[4-[4-(chloromethyl)phenyl]-2-methylbutyryl]amino]-3,3-dimethyl-7-oxo-4-thia-1-azabicyclo[3.2.0]heptane-2-carboxylic acid, 6-[[2-[4-(chloromethyl)phenoxy]acetyl]amino]-3,3-dimethyl-7-oxo-4-thia-1-azabicyclo[3.2.0]heptane-2-carboxylic acid, 6-[[2-[4-(chloromethyl)phenoxy]-2-methylacetyl]amino]-3,3-dimethyl-7-oxo-4-thia-1-azabicyclo[3.2.0]heptane-2-carboxylic acid, 6-[[4-[4-(chloromethyl)phenoxy]-2-methylbutyryl]amino]-3,3-dimethyl-7-oxo-4-thia-1-azabicyclo[3.2.0]heptane-2-carboxylic acid, 6-[[2-[4-(chloromethyl)anilino]acetyl]amino]-3,3-dimethyl-7-oxo-4-thia-1-azabicyclo[3.2.0]heptane-2-carboxylic acid, 6-[[3-[4-(chloromethyl)anilino]-2-methylpropionyl]amino]-3,3-dimethyl-7-oxo-4-thia-1-azabicyclo[3.2.0]heptane-2-carboxylic acid, 6-[[2-[4-(chloromethyl)phenylthio]acetyl]amino]-3,3-dimethyl-7-oxo-4-thia-1-azabicyclo[3.2.0]heptane-2-carboxylic acid, 6-[[2-[2-(chloro)-4-(chloromethyl)phenyl]acetyl]amino]-3,3-dimethyl-7-oxo-4-thia-1-azabicyclo[3.2.0]heptane-2-carboxylic acid, 6-[[4-[4-(chloromethyl)phenylthio]butyryl]amino]-3,3-dimethyl-7-oxo-4-thia-1-azabicyclo[3.2.0]heptane-2-carboxylic acid.

EXAMPLE 24

When in the procedure of Example 17 an appropriate amount of an acid listed in the following Table VI is substituted for p-chloromethylphenylglycine the respective cephalosporin derivatives listed in Table VI are obtained:

TABLE VI

| Acid | Cephalosporin Derivative |
| --- | --- |
| p-(chloromethylphenyl)alanine | 3-[(acetyloxy)methyl]-7-[[3-[4-(chloromethyl)-phenyl]-2-aminopropionyl]amino]-8-oxo-5-thia-1-azabicyclo[4.2.0]oct-2-ene-2-carboxylic acid |
| 2-amino-4-(p-chloromethylphenoxy)-butyric acid | 3-[(acetyloxy)methyl]-7-[[4-[4-(chloromethyl)-phenoxy]-2-aminobutyryl]amino]-8-oxo-5-thia-1-azabicyclo[4.2.0]oct-2-ene-2-carboxylic acid |
| 2-amino-4-(p-chloromethylanilino)-butyric acid | 3-[(acetyloxy)methyl]-7-[[4-[4-(chloromethyl)anilino]-2-aminobutyryl]amino]-8-oxo-5-thia-1-azabicyclo[4.2.0]oct-2-ene-2-carboxylic acid |
| 3-(p-chloromethylphenyl)thioalanine | 3-[(acetyloxy)methyl]-7-[[3-[4-(chloromethyl)-phenylthio]-2-aminopropionyl]amino]-8-oxo-5-thia-1-azabicyclo[4.2.0]oct-2-ene-2-carboxylic acid |
| 2-[2-(5-chloromethyl)thienyl]glycine | 3-[(acetyloxy)methyl]-7-[[2-[5-(chloromethyl)-2-thienyl]-2-aminoacetyl]amino]-8-oxo-5-thia-1-azabicyclo[4.2.0]oct-2-ene-2-carboxylic acid |
| 2-amino-4-[2-(5-chloromethyl)thienyl]-butyric acid | 3-[(acetyloxy)methyl]-7-[[4-[5-(chloromethyl)-2-thienyl]-2-aminobutyryl]amino]-8-oxo-5-thia-1-azabicyclo[4.2.0]oct-2-ene-2-carboxylic acid |

In a similar manner as described in Example 17 when an appropriate amount of 6-amino-3,3-dimethyl-7-oxo-4-thia-1-azabicyclo[3.2.0]heptane-2-carboxylic acid is reacted with an appropriate amount of the acids listed in Table VI the following respective penicillin derivatives are obtained.

6-[[3-[4-chloromethyl)phenyl]-2-aminopropionyl]amino]-3,3-dimethyl-7-oxo-4-thia-1-azabicyclo[3.2.0]heptane-2-carboxylic acid, 6-[[4-[4-(chloromethyl]phenoxy]-2-aminobutyryl]amino]-3,3-dimethyl-7-oxo-4-thia-1-azabicyclo[3.2.0]heptane-2-carboxylic acid, 6-[[4-[4-(chloromethyl]anilino]-2-aminobutyryl]amino-3,3-dimethyl-7-oxo-4-thia-1-azabicyclo[3.2.0-]heptane-2-carboxylic acid, 6-[[3-[4-(chloromethyl]-2-aminopropionyl]amino]-3,3-dimethyl-7-oxo-4-thia-1-azabicyclo[3.2.0]heptane-2-carboxylic acid, 6-[[2-[5-(chloromethyl)-2-thienyl]-2-aminoacetyl]amino]-3,3-dimethyl-7-oxo-4-thia-1-azabicyclo[3.2.0]heptane-2-carboxylic acid, 6-[[4-[5-(chloromethyl)-2-thienyl]-2-aminobutyryl-]amino]-3,3-dimethyl-7-oxo-4-thia-1-azabicyclo[3.2.0]heptane-2-carboxylic acid,

EXAMPLE 25

When in the procedure of Example 19 an appropriate amount of an acid chloride listed in the following Table VII is substituted for 2-chloromethyl-4-methoxymandelic acic chloride the respective cephalosporin derivatives listed in Table VII are obtained:

TABLE VI

| Acid Chloride | Cephalosporin Derivative |
| --- | --- |
| 3-(p-chloromethylphenyl)lactic acid chloride | 3-[(acetyloxy)methyl]-7-[[3-[4-(chloromethyl)-phenyl]-2-hydroxypropionyl]amino]-8-oxo-5-thia-1-azabicyclo[4.2.0]oct-2-ene-2-carboxylic acid |
| 2-hydroxy-4-(p-chloromethylphenyl)butyric acid chloride | 3-[(acetyloxy)methyl]-7-[[4-[4-(chloromethyl)-phenyl]-2-hydroxybutyryl]amino]-8-oxo-5-thia-1-azabicyclo[4.2.0]oct-2-ene-2-carboxylic acid |
| 2-hydroxy-2-[2-(5-chloromethyl)thienyl]-acetic acid chloride | 3-[(acetyloxy)methyl]-7-[[2-[5-(chloromethyl)-2-thienyl]-2-hydroxyacetyl]amino]-8-oxo-5-thia-1-azabicyclo[4.2.0]oct-2-ene-2-carboxylic acid |
| p-chloromethylmandelic acid chloride | 3-[(acetyloxy)methyl]-7-[[2-[4-(chloromethyl)-phenyl]-2-hydroxyacetyl]amino]-8-oxo-5-thia-1-azabicyclo[4.2.0]oct-2-ene-2-carboxylic acid |

In a similar manner as described in Example 19 when an appropriate amount of 6-amino-3,3-dimethyl-7-oxo-4-thia-1-azabicyclo[3.2.0]heptane-2-carboxylic acid is reacted with an appropriate amount of the acid chlorides listed in Table VII the following respective penicillin derivatives are obtained:

6-[[3-[4-(chloromethyl)phenyl]-2-hydroxypropionyl]amino]-3,3-dimethyl-7-oxo-4-thia-1-azabicyclo[3.2.0]heptane-2-carboxylic acid, 6-[[4-[4-(chloromethyl)phenyl]-2-hydroxybutyryl]amino]-3,3-dimethyl-7-oxo-4-thia-1-azabicyclo[3.2.0]heptane-2-carboxylic acid, 6-[[2-[5-(chloromethyl)-2-thienyl]-2-hydroxyacetyl]amino]-3,3-dimethyl-7-oxo-4-thia-1-azabicyclo[3,2.0]heptane-2-carboxylic acid,

EXAMPLE 26

When in the procedure of Example 22 an appropriate amountof of an acid listed in Table VIII is substituted for p-chloromethylphenylmalonic acid the respective cephalosporin derivatives listed in Table VIII are obtained:

4-thia-1-azabicyclo[3.2.0]heptane-2-carboxylic acid is reacted with the acids listed in Table VIII the following respective penicillin derivatives are obtained:

6-[[2-[4-(chloromethyl)phenyl]-2-sulfoacetyl-]amino]-3,3-dimethyl-7-oxo-4-thia-1-azabicyclo[3,2,0]heptane-2-carboxylic acid, 6-[[4-[4-(chloromethyl)phenyl]-2-sulfobutyryl-]amino]-3,3-dimethyl-7-oxo-4-thia-1-azabicyclo[3.2.0]heptane-2-carboxylic acid, 6-[[3-[4-(chloromethyl)phenyl]-2-carboxypropionyl]amino]-3,3-dimethyl-7-oxo-4-thia-1-azabicyclo[3.2.0]heptane-2-carboxylic acid, 6-[[4-[4-(chloromethyl)phenyl]-2-carboxybutyryl]amino]-3,3-dimethyl-7-oxo-4-thia-1-azabicyclo[3.2.0]heptane-2-carboxylic acid, 6-[[4-[4-(chloromethyl)phenylthio]-2-carboxybutyryl]amino]-3,3-dimethyl-7-oxo-4-thia-1-azabicyclo[3.2.0]heptane-2-carboxylic acid, 6-[[3-[4-(chloromethyl)anilino]-2-carboxypropionyl]amino]-3,3-dimethyl-7-oxo-4-thia-1-azabicyclo[3.2.0]heptane-2-carboxylic acid, and 6-[[3-[5-(chloromethyl)-2-thienyl]-2-carboxypropionyl]amino]-3,3-dimethyl-7-oxo-4-thia-1-azabicyclo[3.2.0]heptane-2-carboxylic acid.

EXAMPLE 27

3-[(Acetyloxy)methyl]-7-[[2-[4-(isothioureamethyl)-phenyl]-acetyl]amino]-8-oxo-5-thia-1-azabicyclo[4.2.-0]oct-2-ene-2-carboxylic acid hydrochloride A warm solution of 0.12 g of 3-[(acetyloxy)methyl]-7-[[2-[4-(chloromethyl)phenyl]acetyl]amino]-8-oxo-5-thia-1-azabicyclo[4.2.0]oct-2-ene-2-carboxylic acid

TABLE VIII

| Acid | Cephalosporin Derivative |
| --- | --- |
| 2-sulfo-p-chloromethylphenylacetic acid | 3-[(acetyloxy)methyl]-7-[[2-[4-(chloromethyl)-phenyl]-2-sulfoacetyl]amino]-8-oxo-5-thia-1-azabicyclo[4.2.0]oct-2-ene-2-carboxylic acid |
| 4-(p-chloromethylphenyl)-2-sulfobutyric acid | 3-[(acetyloxy)methyl]-7-[[4-[4-(chloromethyl)-phenyl]-2-sulfobutyryl]amino]-8-oxo-5-thia-1-azabicyclo[4.2.0]oct-2-ene-2-carboxylic acid |
| p-chloromethylbenzylmalonic acid | 3-[(acetyloxy)methyl]-7-[[3-[4-(chloromethyl)-phenyl]-2-carboxypropionyl]amino]-8-oxo-5-thia-1-azabicyclo[4.2.0]oct-2-ene-2-carboxylic acid |
| 2-(p-chloromethylphenoxy)ethylmalonic acid | 3-[(acetyloxy)methyl]-7-[[4-[4-(chloromethyl)-phenoxy]-2-carboxybutyryl]amino]-8-oxo-5-thia-1-azabicyclo[4.2.0]oct-2-ene-2-carboxylic acid |
| 2-(p-chloromethylphenyl)thioethylmalonic acid | 3-[(acetyloxy)methyl]-7-[[4-[4-(chloromethyl)-phenylthio]-2-carboxybutyryl]amino]-8-oxo-5-thia-1-azabicyclo[4.2.0]oct-2-ene-2-carboxylic acid |
| p-chloromethylanilinomethylmalonic acid | 3-[(acetyloxy)methyl]-7-[[3-[4-(chloromethyl)-anilino]-2-carboxypropionyl]amino]-8-oxo-5-thia-1-azabicyclo[4.2.0]oct-2-ene-2-carboxylic acid |
| 2-[2-(5-chloromethyl)thenyl]malonic acid | 3-[(acetyloxy)methyl]-7-[[3-[5-(chloromethyl)-2-thienyl]-2-carboxypropionyl]amino]-8-oxo-5-thia-1-azabicyclo[4.2.0]oct-2-ene-2-carboxylic acid |

In a similar manner as described in Example 22 when an appropriate amount of 6-amino-3,3-dimethyl-7-oxoand 0.12 g of isothiourea in 30 ml of ethanol is refluxed for 4 hours after which the solvent is removed under high vacuum at room temperature yielding an oil which is triturated with 80 ml of benzene-acetone (2:1) to give 3-[(acetyloxy)methyl]-7-[[2-[4-(isothioureamethyl)phenyl]acetyl]amino]-8-oxo-5-thia-1-azabicyclo[4.2.0]oct-2-ene-2-carboxylic acid hydrochloride.

In a similar manner when the halomethylated derivatives and the isothiourea derivatives listed in the following Table IX are reacted the respective products listed in Table IX are obtained.

TABLE IX

| Halomethylated Derivative | Isothiourea Derivative | Product |
|---|---|---|
| 3-[(acetyloxy)methyl]-7-[[2-[4-(chloromethyl)phenyl]acetyl]amino]-8-oxo-5-thia-1-azabicyclo[4.2.0]-oct-2-ene-2-carboxylic acid acetyloxymethyl ester | isothiourea | 3-[(acetyloxy)methyl]-7-[[2-[4-(isothioureamethyl)phenyl]acetyl]amino]-8-oxo-5-thia-1-azabicyclo[4.2.0]-oct-2-ene-2-carboxylic acid acetyloxymethyl ester |
| 3-[(acetyloxy)methyl]-7-[[2-[4-(chloromethyl)phenyl]acetyl]amino]-8-oxo-5-thia-1-azabicyclo[4.2.0]-oct-2-ene-2-carboxylic acid propionyloxymethyl ester | isothiourea | 3-[(acetyloxy)methyl]-7-[[2-[4-(isothioureamethyl)phenyl]acetyl]amino]-8-oxo-5-thia-1-azabicyclo[4.2.0]-oct-2-ene-2-carboxylic acid propionyloxymethyl ester |
| 3-[(acetyloxy)methyl]-7-[[2-[4-(chloromethyl)phenyl]acetyl]amino]-8-oxo-5-thia-1-azabicyclo[4.2.0]-oct-2-ene-2-carboxylic acid butyryloxymethyl ester | 1,1,3-triethyl-isothiourea | 3-[(acetyloxy)methyl]-7-[[2-[4-(1,1,3-triethylisothioureamethyl)phenyl]acetyl]amino]-8-oxo-5-thia-1-azabicyclo[4.2.0]-oct-2-ene-2-carboxylic acid butyryloxymethyl ester |
| 3-[(acetyloxy)methyl]-7-[[2-[4-(chloromethyl)phenyl]acetyl]amino]-8-oxo-5-thia-1-azabicyclo[4.2.0]-oct-2-ene-2-carboxylic acid pivalyloxymethyl ester | isothiourea | 3-[(acetyloxy)methyl]-7-[[2-[4-(isothioureamethyl)phenyl]acetyl]amino]-8-oxo-5-thia-1-azabicyclo[4.2.0]-oct-2-ene-2-carboxylic acid pivalyloxymethyl ester |
| 3-(2-methyl-1,3,4-thiadiazol-5-yl-thio)-7-[[2-[4-(chloromethyl)phenyl]-acetyl]amino]-8-oxo-5-thia-1-azibicyclo[4.2.0]oct-2-ene-2-carboxylic acid propionyloxymethyl ester | isothiourea | 3-(2-methyl-1,3,4-thiadiazol-5-yl-thio)-7-[[2-[4-(isothioureamethyl)-phenyl]acetyl]amino]-8-oxo-5-thia-1-azabicyclo[4.2.0]oct-2-ene-2-carboxylic acid propionyloxymethyl ester |
| 3-(2-methyl-1,3,4-thiadiazol-5-yl-thio)-7-[[2-[4-(chloromethyl)phenyl]-acetyl]amino]-8-oxo-5-thia-1-azabicyclo[4.2.0]oct-2-ene-2-carboxylic acid pivalyloxymethyl ester | isothiourea | 3-(2-methyl-1,3,4-thiadiazol-5-yl-thio)-7-[[2-[4-(isothioureamethyl)-phenyl]acetyl]amino]-8-oxo-5-thia-1-azabicyclo[4.2.0]oct-2-ene-2-carboxylic acid pivalyloxymethyl ester |
| 3-(1-methyltetrazol-5-ylthio)-7-[[2-[4-(chloromethyl)phenyl]acetyl]amino]-8-oxo-5-thia-1-azabicyclo[4.2.0]-oct-2-ene-2-carboxylic acid | n-propylisothiourea | 3-(1-methyltetrazol-5-ylthio)-7-[[2-[4-(n-propylisothioureamethyl)phenyl]acetyl]-amino]-8-oxo-5-thia-1-azabicyclo[4.2.0]-oct-2-ene-2-carboxylic acid |
| 6-[[2-[4-(chloromethyl)phenyl]-acetyl]amino]-3,3-dimethyl-7-oxo-4-thia-1-azabicyclo[3.2.0]-heptane-2-carboxylic acid | 1-ethyl-3-n-propylisothiourea | 6-[[2-[4-(1-ethyl-3-n-propylisothioureamethyl)phenyl]acetyl]amino]-3,3-dimethyl)-7-oxo-4-thia-1-azabicyclo-[3.2.0]heptane-2-carboxylic acid |
| 3-[(acetyloxy)methyl]-7-[[2-[2-(chloromethyl)-4-methoxyphenyl]-2-hydroxyacetyl]amino]-8-oxo-5-thia-1-azabicyclo[4.2.0]oct-2-ene-2-carboxylic acid | isothiourea | 3-[(acetyloxy)methyl]-7-[[2-[2-isothioureamethyl)-4-methoxyphenyl)-2-hydroxyacetyl]amino]-8-oxo-5-thia-1-azabicyclo[4.2.0]oct-2-ene-2-carboxylic acid |
| 6-[[2-[2-(chloromethyl)-4-methoxyphenyl]-2-hydroxyacetyl]amino]-3,3-dimethyl-7-oxo-4-thia-1-azabicyclo[3.2.0]heptane-2-carboxylic acid | isothiourea | 6-[[2-[2-(isothioureamethyl)-4-methoxyphenyl]-2-hydroxyacetyl]amino]-3,3-dimethyl-7-oxo-4-thia-1-azabicyclo[3.2.0]heptane-2-carboxylic acid |
| 3-[(acetyloxy)methyl]-7-[[2-[5-(chloromethyl)-2-thienyl]acetyl)-amino]-8-oxo-5-thia-1-azabicyclo-[4.2.0]oct-2-ene-2-carboxylic acid | isothiourea | 3-[(acetyloxy)methyl]-7-[[2-[5-isothioureamethyl)-2-thienyl]acetyl]-amino]-8-oxo-5-thia-1-azabicyclo-[4.2.0]oct-2-ene-2-carboxylic acid |
| 3-[(acetyloxy)methyl]-7-[[2-[4-(chloromethyl)phenyl]-2-carboxyacetyl]amino]-8-oxo-5-thia-1-azabicyclo[4.2.0]oct-2-ene-2-carboxylic acid | isothiourea | 3-[(acetoxy)methyl]-7-[[2-[4-isothioureamethyl)phenyl]-2-carboxyacetyl]amino]-8-oxo-5-thia-1-azabicyclo[4.2.0]oct-2-ene-2-carboxylic acid |
| 3-[acetyloxy)methyl]-7-[[2-[4-(chloromethyl)phenyl]-2-methyl-acetyl]amino]-8-oxo-5-thia-1-azabycyclo[4.2.0]oct-2-ene-2-carboxycilic acid | 1,1-diethyl-3-methylisothiourea | 3-[(acetyloxy)methyl]-7-[[2-[4-(1,1-diethyl-3-methylisothioureamethyl)-phenyl]-2-methylacetyl]amino]-8-oxo-5-thia-1-azabicyclo[4.2.0]oct-2-ene-2-carboxylic acid |
| 3-[(acetyloxy)methyl]-7-[[3-[4-(chloromethyl)phenyl]propionyl]-amino]-8-oxo-5-thia-1-azabicyclo-[4.2.0]oct-2-ene-2-carboxylic acid | 1-ethyl-3-methyl isothiourea | 3-[(acetyloxy)methyl]-7-[[3-[4-(1-ethyl-3-methylisothioureamethyl)-phenyl]propionyl]amino]-8-oxo-5-thia-1-azabicyclo[4.2.0]oct-2-ene-2-carboxylic acid |
| 3-[(acetyloxy)methyl]-7-[[3-[4- | isothiourea | 3-[(acetyloxy)methyl]-7-[[3-[4-(iso- |

TABLE IX-continued

| Halomethylated Derivative | Isothiourea Derivative | Product |
|---|---|---|
| (chloromethyl)phenyl]-2-methylpropionyl]amino]-8-oxo-5-thia-1-azabicyclo[4.2.0]oct-2-ene-2-carboxylic acid | | thioureamethyl)phenyl]-2-methylpropionyl]amino]-8-oxo-5-thia-1-azabicyclo[4.2.0]oct-2-ene-2-carboxylic acid |
| 3-[(acetyloxy)methyl]-7-[[2-[4-(chloromethyl)phenyl]acetyl]amino]-8-oxo-5-thia-1-azabicyclo[4.2.0]-oct-2-ene-2-carboxylic acid acetyloxymethyl ester | isothiourea | 3-[(acetyloxy)methyl]-7-[[2-[4-isothioureamethyl)phenyl]acetyl]amino]-8-oxo-5-thia-1-azabicyclo[4.2.0]oct-2-ene-2-carboxylic acid acetyloxymethyl ester |
| 3-[(acetyloxy)methyl]-7-[[2-[4-(chloromethyl)phenoxy]acetyl]amino]-8-oxo-5-thia-1-azabicyclo[4.2.0]-oct-2-ene-2-carboxylic acid | isothiourea | 3-[(acetyloxy)methyl]-7-[[2-[4-(isothioureamethyl)phenoxy]acetyl]amino]-8-oxo-5-thia-1-azabicyclo[4.2.0]oct-2-ene-2-carboxylic acid |
| 3-[(acetyloxy)methyl]-7-[[2-[4-(chloromethyl)phenoxy]2-methylacetyl]amino]-8-oxo-5-thia-1-azabicyclo[4.2.0]oct-2-ene-2-carboxylic acid | 1-n-butyl-3-methylisothiourea | 3-[(acetyloxy)methyl]-7-[[2-[4-(1-n-butyl-3-methylisothioureamethyl)-phenoxy]2-methylacetyl]amino]-8-oxo-5-thia-1-azabicyclo[4.2.0]oct-2-ene-2-carboxylic acid |
| 3-[(acetyloxy)methyl]-7-[[2-[4-(chloromethyl)phenyl]acetyl]amino]-8-oxo-5-thia-1-azabicyclo[4.2.0]-oct-2-ene-2-carboxylic acid propionyloxybenzyl ester | 1,3-di-n-propyl-isothiourea | 3-[(acetyloxy)methyl]-7-[[2-[4-(1,3-di-n-propylisothioureamethyl)phenyl]-acetyl]amino]-8-oxo-5-thia-1-azabicyclo-[4.2.0]oct-2-ene-2-carboxylic acid propionyloxybenzyl ester |
| 3-[(acetyloxy)methyl]-7-[[2-[4-(chloromethyl)anilino]acetyl]-amino]-8-oxo-5-thia-1-azabicyclo-[4.2.0]oct-2-ene-2-carboxylic acid | 1,3-diisopropyl-isothiourea | 3-[(acetyloxy)methyl]-7-[[2-[4-(1,3-diisopropylisothioureamethyl)anilino]-acetyl]amino]-8-oxo-5-thia-1-azabicyclo[4.2.0]oct-2-ene-2-carboxylic acid |
| 3-[(acetyloxy)methyl]-7-[[3-[4-(chloromethyl)anilino]-2-methylpropionyl]amino]-8-oxo-5-thia-1-azabicyclo[4.2.0]oct-2-ene-2-carboxylic acid | isothiourea | 3-[(acetyloxy)methyl]-7-[[3-[4-(isothioureamethyl)anilino]-2-methylpropionyl]amino]-8-oxo-5-thia-1-azabicyclo[4.2.0]oct-2-ene-2-carboxylic acid |
| 3-[(acetyloxy)methyl]-7-[[2-[4-(chloromethyl)phenylthio]acetyl]-amino]-8-oxo-5-thia-1-azabicyclo-[4.2.0]oct-2-ene-2-carboxylic acid | isothiourea | 3-[(acetyloxy)methyl]-7-[[2-[4-(isothioureamethyl)phenylthio]acetyl]-amino]-8-oxo-5-thia-1-azabicyclo-[4.2.0]oct-2-ene-2-carboxylic acid |
| 3-[(acetyloxy)methyl]-7-[[2-[2-(chloro)-4-(chloromethyl)phenyl]-acetyl]amino]-8-oxo-5-thia-1-azabicyclo[4.2.0]oct-2-ene-2-carboxylic acid | isothiourea | 3-[(acetyloxy)methyl]-7-[[2-[2-(chloro)-4-(isothioureamethyl)phenyl]acetyl]amino]-8-oxo-5-thia-1-azabicyclo[4.2.0]-oct-2-ene-2-carboxylic acid |
| 3-[(acetyloxy)methyl]-7-[[4-[4-(chloromethyl)phenylthio]butyryl]-amino]-8-oxo-5-thia-1-azabicyclo-[4.2.0]oct-2-ene-2-carboxylic acid | 3-n-propylisothiourea | 3-[(acetyloxy)methyl]-7-[[4-[4-(3-n-propylisothioureamethyl)phenylthio]-butyryl]amino]-8-oxo-5-thia-1-azabicyclo[4.2.0]oct-2-ene-2-carboxylic acid |
| 3-[(acetyloxy)methyl]-7-[[2-[4-(chloromethyl)phenyl]acetyl]amino]-8-oxo-5-thia-1-azabicyclo[4.2.0]oct-2-ene-2-carboxylic acid 2-amino-3-methylbutyryloxymethyl ester | isothiourea | 3-[(acetyloxy)methyl]-7-[[2-[4-(isothioureamethyl)phenyl]acetyl]amino]-8-oxo-5-thia-1-azabicyclo[4.2.0]oct-2-ene-2-carboxylic acid 2-amino-3-methylbutyryloxymethyl ester |
| 3-[(acetyloxy)methyl]-7-[[2-[4-(chloromethyl)phenyl]acetyl]amino]-8-oxo-5-thia-1-azabicyclo[4.2.0]oct-2-ene-2-carboxylic acid pivalyloxymethyl ester | 1-ethylisothiourea | 3-[(acetyloxy)methyl]-7-[[2-[4-(1-ethylisothioureamethyl)phenyl]acetyl]-amino]-8-oxo-5-thia-1-azabicyclo[4.2.0]-oct-2-ene-2-carboxylic acid pivalyloxymethyl ester |
| 6-[[3-[4-(chloromethyl)phenyl]-2-methylpropionyl]amino]-3,3-dimethyl-7-oxo-4-thia-1-azabicyclo[3.2.0]heptane-2-carboxylic acid | 1,3-diethylisothiourea | 6-[[3-[4-(1,3-diethylisothioureamethyl)-phenyl]-2-methylpropionyl]amino]-3,3-dimethyl-7-oxo-4-thia-1-azabicyclo-[3.2.0]heptane-2-carboxylic acid |
| 6-[[4-[4-(chloromethyl)phenyl]-2-methylbutyryl]amino]-3,3-dimethyl-7-oxo-4-thia-1-azabicyclo[3.2.0]heptane-2-carboxylic acid | 1,1-dimethyl-3-ethyl-isothiourea | 6-[[4-[4-(1,1-dimethyl-3-ethylisothioureamethyl)phenyl]-2-methylbutyryl]-amino]-3,3-dimethyl-7-oxo-4-thia-1-azabicyclo[3.2.0]heptane-2-carboxylic acid |
| 6-[[2-[4-(chloromethyl)phenoxy]acetyl]-amino]-3,3-dimethyl-7-oxo-4-thia-1-azabicyclo[3.2.0]heptane-2-carboxylic acid | isothiourea | 6-[[2-[4-(isothioureamethyl)phenoxy]-acetyl]amino]-3,3-dimethyl-7-oxo-4-thia-1-azabicyclo[3.2.0]heptane-2-carboxylic acid |
| 6-[[2-[4-(chloromethyl)phenoxy]-2-methylacetyl]amino]-3,3-dimethyl-7-oxo-4-thia-1-azabicyclo[3.2.0]heptane-2-carboxylic acid | isothiourea | 6-[[2-[4-(isothioureamethyl)phenoxy]-2-methylacetyl]amino]3,3-dimethyl-7-oxo-4-thia-1-azabicyclo[3.2.0]heptane-2-carboxylic acid |

TABLE IX-continued

| Halomethylated Derivative | Isothiourea Derivative | Product |
|---|---|---|
| 3-(2-methyl-1,3,4-thiadiazol-5-yl thio]-7-[[2-[4-(chloromethyl)phenyl]-acetyl]amino]-8-oxo-5-thia-1-azabicy-clo[4.2.0]amino]-8-oxo-5-thia-1-azabi-cyclo[4.2.0]oct-2-ene-2-carboxylic acid | isothiourea | 3-(2-methyl-1,3,4-thiadiazol-5-ylthio]-7-[[2-[4-isothioureamethyl)phenyl]ace-tyl]amino]-8-oxo-5-thia-1-azabicyclo-[4.2.0]oct-2-ene-2-carboxylic acid |
| 6-[[2-[4-(chloromethyl)anilino]-acetyl]amino]-3,3-dimethyl-7-oxo-4-thia-1-azabicyclo[3.2.0]heptane-2-carboxylic acid | 1-methyl-3-ethyl-isothiourea | 6-[[2-[4-(1-methyl-3-ethyl-isothio-ureamethyl)anilino]acetyl]amino]-3,3-dimethyl-7-oxo-4-thia-1-azabicyclo-[3.2.0]heptane-2-carboxylic acid |
| 6-[[3-[4-(chloromethyl)anilino]-2-methylpropionyl]amino]-3,3-di-methyl-7-oxo-4-thia-1-azabicyclo-[3.2.0]heptane-2-carboxylic acid | isothiourea | 6-[[3-[4-(isothioureamethyl)anilino]-2-methylpropionyl]amino]-3,3-dimethyl-7-oxo-4-thia-1-azabicyclo[3.2.0]hep-tane-2-carboxylic acid |
| 6-[[2-[4-(chloromethyl)phenylthio]-acetyl]amino]-3,3-dimethyl-7-oxo-4-thia-1-azabicyclo[3.2.0]heptane-2-carboxylic acid | 1,3-di-n-butyl-isothiourea | 6-[[2-[4-(1,3-di-n-butylisothiourea-methyl)phenylthio]acetyl]amino]-3,3-dimethyl-7-oxo-4-thia-1-azabicyclo-[3.2.0]heptane-2-carboxylic acid |
| 6-[[2-[2-(chloro)-4-(chloromethyl)-phenyl]acetyl]amino]-3,3-dimethyl-7-oxo-4-thia-1-azabicyclo[3.2.0]-heptane-2-carboxylic acid | isothiourea | 6-[[2-[2-(chloro-4-(isothioureamethyl)-phenyl]acetyl]amino]-3,3-dimethyl-7-oxo-4-thia-1-azabicyclo[3.2.0]heptane-2-carboxylic acid |
| 6-[[4-[4-(chloromethyl)phenyl-thio]butyryl]amino]-3,3-dimethyl-7-oxo-4-thia-1-azabicyclo[3.2.0]-heptane-2-carboxylic acid | 1,1-diethyl-3-methylisothiourea | 6-[[4-[4-(1,1-diethyl-3-methyliso-thioureamethyl)phenylthio]butyryl]-amino]-3,3-dimethyl-7-oxo-4-thia-1-azabicyclo[3.2.0]heptane-2-carboxylic acid |
| 3-[(acetyloxy)methyl]-7-[[3-[4-(chloromethyl)phenyl]-2-hydroxy-propionyl]amino]-8-oxo-5-thia-1-azabicyclo[4.2.0]oct-2-ene-2-carboxylic acid | 1,3-diethylisothiourea | 3-[(acetyloxy)methyl]-7-[[3-[4-(1,3-diethylisothioureamethyl)phenyl]-2-hydroxypropionyl]amino]-8-oxo-5-thia-1-azabicyclo[4.2.0] oct-2-ene-2-carboxylic acid |
| 3-[(acetyloxy)methyl]-7-[[4-[4-(chloromethyl)phenyl]-2-hydroxy-butyryl]amino]-8-oxo-5-thia-1-azabicyclo[4.2.0]oct-2-ene-2-carboxylic acid | 1-ethylisothiourea | 3-[(acetyloxy)methyl]-7-[[4-[4-(1-ethylisothioureamethyl)phenyl]-2-hydroxybutyryl]amino]-8-oxo-5-thia-1-azabicyclo[4.2.0]oct-2-ene-2-carbox-ylic acid |
| 3-[(acetyloxy)methyl]-7-[[2-[5-(chloromethyl)-2-thienyl]-2-hydroxyacetyl]amino]-8-oxo-5-thia-1-azabicyclo[4.2.0]oct-2-ene-2-carboxylic acid | 3-n-propylisothiourea | 3-[(acetyloxy)methyl]-7-[[2-[5-(3-n-propylisothioureamethyl)-2-thienyl]-2-hydroxyacetyl]amino]-8-oxo-5-thia-1-azabicyclo[4.2.0]oct-2-ene-2-carboxylic acid |
| 6-[[3-[4-(chloromethyl)phenyl]-2-hydroxypropionyl]amino]-3,3-dimethyl-7-oxo-4-thia-1-azabicy-clo[3.2.0]heptane-2-carboxylic acid | 1,3-dimethyliso-thiourea | 6-[[3-[4-(1,3-dimethylisothiourea-methyl)phenyl]-2-hydroxypropionyl]-amino]-3,3-dimethyl-7-oxo-4-thia-1-azabicyclo[3.2.0]heptane-2-carboxylic acid |
| 3-(1-methyltetrazol-5-ylthio)-7-[[2-[4-(chloromethyl)phenyl]acetyl]-amino]-8-oxo-5-thia-1-azabicyclo-[4.2.0]oct-2-ene-2-carboxylic acid | isothiourea | 3-(1-methyltetrazol-5-ylthio)-7-[[2-[4-isothioureamethyl)phenyl]acetyl]amino]-8-oxo-5-thia-1-azabicyclo[4.2.0]oct-2-ene-2-carboxylic acid |
| 6-[[2-[5-(chloromethyl)-2-thienyl]-2-hydroxyacetyl]amino]-3,3-dimethyl-7-oxo-4-thia-1-azabicyclo[3.2.0]-heptane-2-carboxylic acid | 1,3-di-n-butyl-isothiourea | 6-[[2-[5-(1,3-di-n-butylisothiourea-methyl)-2-thienyl]-2-hydroxyacetyl]-amino]-3,3-dimethyl-7-oxo-4-thia-1-azabicyclo[3.2.0]heptane-2-carboxylic acid |
| 3-[(acetyloxy)methyl]-7-[[2-[4-(chloromethyl)phenyl]-2-sulfo-acetyl]amino]-8-oxo-5-thia-1-azabicyclo[4.2.0]oct-2-ene-2-carboxylic acid | 1-methyl-3-ethyl-isothiourea | 3-[(acetyloxy)methyl]-7-[[2-[4-(1-methyl-3-ethylisothioureamethyl)-phenyl]-2-sulfoacetyl]amino]-8-oxo-5-thia-1-azabicyclo[4.2.0]oct-2-ene-2-carboxylic acid |
| 3-[(acetyloxy)methyl]-7-[[4-[4-(chloromethyl)phenyl]-2-sulfo-butyryl]amino]-8-oxo-5-thia-1-azabicyclo[4.2.0]oct-2-ene-2-car-boxylic acid | 1-ethyl-3-isopro-pylisothiourea | 3-[(acetyloxy)methyl]-7-[[4-[4-(1-ethyl-3-isopropylisothioureamethyl)-phenyl]-2-sulfobutyryl]amino]-8-oxo-5-thia-1-azabicyclo[4.2.0]oct-2-ene-2-carboxylic acid |
| 3-[(acetyloxy)methyl]-7-[[3-[4-(chloromethyl)phenyl]-2-carboxypro-pionyl]amino]-8-oxo-5-thia-1-aza-bicyclo[4.2.0]oct-2-ene-2-car-boxylic acid | 1,1,3-triethyl-isothiourea | 3-[(acetyloxy)methyl]-7-[[3-[4-(1,1,3-triethylisothioureamethyl)phenyl]-2-carboxypropionyl]amino]-8-oxo-5-thia-1-azabicyclo[4.2.0]oct-2-ene-2-car-boxylic acid |
| 3-[(acetyloxy)methyl]-7-[[4-[4-(chloromethyl)phenoxy]-2-carboxy-butyryl]amino]-8-oxo-5-thia-1-azabicyclo[4.2.0]oct-2-ene-2-carboxylic acid | 1,1-di-n-propyl-3-methylisothiourea | 3-[(acetyloxy)methyl]-7-[[4-[4-(1,1-di-n-propyl-3-methylisothioureamethyl)-phenoxy]-2-carboxybutyryl]amino]-8-oxo-5-thia-1-azabicyclo[4.2.0]oct-2-ene-2-carboxylic acid |

TABLE IX-continued

| Halomethylated Derivative | Isothiourea Derivative | Product |
| --- | --- | --- |
| 3-[(acetyloxy)methyl]-7-[[4-[4-(chloromethyl)phenylthio]-2-carboxybutyryl]amino]-8-oxo-5-thia-1-azabicyclo[4.2.0]oct-2-ene-2-carboxylic acid | 1,3-di-sec-butyl-isothiourea | 3-[(acetyloxy)methyl]-7-[[4-[4-(1,3-di-sec-butylisothioureamethyl)phenylthio]-2-carboxybutyryl]amino]-8-oxo-5-thia-1-azabicyclo[4.2.0]oct-2-ene-2-carboxylic acid |
| 3-[(acetyloxy)methyl]-7-[[3-[4-(chloromethyl)anilino]-2-carboxypropionyl]amino]-8-oxo-5-thia-1-azabicyclo[4.2.0]oct-2-ene-2-carboxylic acid | 1,3-di-n-propylisothiourea | 3-[(acetyloxy)methyl]-7-[[3-[4-(1,3-di-n-propylisothioureamethyl)anilino]-2-carboxypropionyl]amino]-8-oxo-5-thia-1-azabicyclo[4.2.0]oct-2-ene-2-carboxylic acid |
| 3-[(acetyloxy)methyl]-7-[[3-[5-(chloromethyl)-2-thienyl]-2-carboxypropionyl]amino]-8-oxo-5-thia-1-azabicyclo[4.2.0]oct-2-ene-2-carboxylic acid | 1-n-butyl-3-methyl-isothiourea | 3-[(acetyloxy)methyl]-7-[[3-[5-(1-n-butyl-3-methylisothioureamethyl)-2-thienyl]-2-carboxypropionyl]amino]-8-oxo-5-thia-1-azabicyclo[4.2.0]oct-2-ene-2-carboxylic acid |
| 6-[[2-[4-(chloromethyl)phenyl]-2-sulfoacetyl]amino]-3,3-dimethyl-7-oxo-4-thia-1-azabicyclo[3.2.0]-heptane-2-carboxylic acid | 1-ethyl-3-methyl-isothiourea | 6-[[2-[4-(1-ethyl-3-methylisothioureamethyl)phenyl]2-sulfoacetyl]amino]-3,3-dimethyl-7-oxo-4-thia-1-azabicyclo[3.2.0]-heptane-2-carboxylic acid |
| 6-[[4-[4-(chloromethyl)phenyl]-2-sulfobutyryl]amino]-3,3-dimethyl-7-oxo-4-thia-1-azabicyclo[3.2.0]-heptane-2-carboxylic acid | isothiourea | 6-[[4-[4-(isothioureamethyl)phenyl]-2-sulfobutyryl]amino]-3,3-dimethyl-7-oxo-4-thia-1-azabicyclo[3.2.0]heptane-2-carboxylic acid |
| 6-[[3-[4-(chloromethyl)phenyl]-2-carboxypropionyl]amino]-3,3-dimethyl-7-oxo-4-thia-1-azabicyclo[3.2.0]-heptane-2-carboxylic acid | 1-ethyl-3-n-propyl-isothiourea | 6-[[3-[4-(1-ethyl-3-n-propylisothioureamethyl)phenyl]-2-carboxypropionyl]amino]-3,3-dimethyl-7-oxo-4-thia-1-azabicyclo[3.2.0]heptane-2-carboxylic acid |
| 6-[[4-[4-(chloromethyl)phenoxy]-2-carboxybutyryl]amino]-3,3-dimethyl-7-oxo-4-thia-1-azabicyclo[3.2.0]-heptane-2-carboxylic acid | 1-ethyl-3-n-butyl-isothiourea | 6-[[4-[4-(1-ethyl-3-n-butylisothioureamethyl)phenoxy]-2-carboxybutyryl]amino]-3,3-dimethyl-7-oxo-4-thia-1-azabicyclo[3.2.0]heptane-2-carboxylic acid |
| 6-[[4-[4-(chloromethyl)phenylthio]-2-carboxybutyryl]amino]-3,3-dimethyl-7-oxo-4-thia-1-azabicyclo[3.2.0]heptane-2-carboxylic acid | 1,1-di-n-propyl-3-ethylisothiourea | 6-[[4-[4-(1,1-di-n-propyl-3-ethylisothioureamethyl)phenylthio]-2-carboxybutyryl]amino]-3,3-dimethyl-7-oxo-4-thia-1-azabicyclo[3.2.0]heptane-2-carboxylic acid |
| 3-(2-methyl-1,3,4-thiadiazol-5-ylthio)-7-[[2-[4-(chloromethyl)phenyl]-2-hydroxyacetyl]amino]-8-oxo-5-thia-1-azabicyclo[4.2.0]oct-2-ene-2-carboxylic acid | isothiourea | 3-(2-methyl-1,3,4-thiadiazol-5-ylthio)-7-[[2-[4-(isothioureamethyl)phenyl]-2-hydroxyacetyl]amino]-8-oxo-5-thia-1-azabicyclo[4.2.0]oct-2-ene-2-carboxylic acid |
| 3-(1-methyltetrazol-5-ylthio)-7-[[2-[4-(chloromethyl)phenyl]-2-hydroxyacetyl]amino]-8-oxo-5-thia-1-azabicyclo[4.2.0]oct-2-ene-2-carboxylic acid | isothiourea | 3-(1-methyltetrazol-5-ylthio)-7-[[2-[4-(isothioureamethyl)phenyl]-2-hydroxyacetyl]amino]-8-oxo-5-thia-1-azabicyclo[4.2.0]oct-2-ene-2-carboxylic acid |
| 3-(2-methyl-1,3,4-thiadiazol-5-ylthio)-7-[[2-[4-(chloromethyl)phenyl]-2-carboxyacetyl]amino]-8-oxo-5-thia-1-azabicyclo[4.2.0]oct-2-ene-2-carboxylic acid | isothiourea | 3-(2-methyl-1,3,4-thiadiazol-5-ylthio)-7-[[2-[4-(isothioureamethyl)phenyl]-2-carboxyacetyl]amino]-8-oxo-5-thia-1-azabicyclo[4.2.0]oct-2-ene-2-carboxylic acid |
| 3-[(acetyloxy)methyl]-7-[[2-[4-(chloromethyl)phenyl]-2-carboxyacetyl]amino]-8-oxo-5-thia-1-azabicyclo[4.2.0]oct-2-ene-2-carboxylic acid | isothiourea | 3-[(acetyloxy)methyl]-7-[[2-[4-(isothioureamethyl)phenyl]-2-carboxyacetyl]amino]-8-oxo-5-thia-1-azabicyclo[4.2.0]oct-2-ene-2-carboxylic acid |
| 3-(1-methyltetrazol-5-ylthio)-7-[[2-[4-(chloromethyl)phenyl]-2-carboxyacetyl]amino]-8-oxo-5-thia-1-azabicyclo[4.2.0]oct-2-ene-2-carboxylic acid pivalyloxybenzyl ester | isothiourea | 3-(1-methyltetrazol-5-ylthio)-7-[[2-[4-(isothioureamethyl)phenyl]-2-carboxyacetyl]amino]-8-oxo-5-thia-1-azabicyclo[4.2.0]oct-2-ene-2-carboxylic acid pivalyloxybenzyl ester |
| 3-[(acetyloxy)methyl]-7-[[2-[4-(chloromethyl)phenyl]-2-hydroxyacetyl]amino]-8-oxo-5-thia-1-azabicyclo[4.2.0]oct-2-ene-2-carboxylic acid | isothiourea | 3-[(acetyloxy)methyl]-7-[[2-[4-(isothioureamethyl)phenyl]-2-hydroxyacetyl]amino]-8-oxo-5-thia-1-azabicyclo[4.2.0]oct-2-ene-2-carboxylic acid |
| 7-[[2-[4-(chloromethyl)phenyl]acetyl]amino]-3-methyl-8-oxo-5-thia-1-azabicyclo[4.2.0]oct-2-ene-2-carboxylic acid | isothiourea | 7-[[2-[4-(isothioureamethyl)phenyl]acetyl]amino]-3-methyl-8-oxo-5-thia-1-azabicyclo[4.2.0]oct-2-ene-2-carboxylic acid |

EXAMPLE 28

3-[(Acetyloxy)methyl]-7-[[2-[4-(isothioureamethyl)-phenyl]-2-aminoacetyl]amino]-8-oxo-5-thia-1-azabicyclo[4.2.0]oct-2-ene-2-carboxylic acid A. A mixture of 7.5 g of 3-[(acetyloxy)methyl]-7-[[2-[4-(chloromethyl)phenyl]-2-aminoacetyl]amino]-8-oxo-5-thia-1-azabicyclo[4.2.0]oct-2-ene-2-carboxylic acid wherein the 2-amino group is protected with hydrochloride salt and 1.03 g of isothiourea in 50 ml of ethanol is heated for several hours at reflux after which the solvent is removed in vacuo at room temperature yielding an oil. The oil is triturated with 2:1 benzene-acetone to give the corresponding isothioureamethyl derivative.

B. At 0° C 10 ml of trifluoroacetic acid is added to 5g of 3-[(acetyloxy)methyl]-7-[[2-[4-(isothioureamethyl)phenyl]-2-aminoacetyl]amino]-8-oxo-5-thia-1-azabicyclo[4.2.0]oct-2-ene-2-carboxylic acid wherein the 2-amino group is protected with tert-butoxycarbonyl obtained in (A) above. The mixture is stirred for several minutes under a nitrogen atmosphere resulting in a clear solution which is stirred an additional 15 minutes at room temperature. The excess trifluoroacetic acid is removed in vacuo, and the remaining residue is triturated with diethylether then dissolved in 175 ml of water. The solution is filtered and the pH of the filtrate adjusted to 5.5 by adding Amberlite IR4B resin that had been washed several times with water. The resin is filtered off and the water concentrated in vacuo. A precipitate forms from the concentrate which is removed and washed with ethanol to give 3-[(acetyloxy)methyl]-7-[[2-[4-(isothioureamethyl)-phenyl]-2-aminoacetyl]amino]-8-oxo-5-thia-1-azabicyclo[4.2.0]oct-2-ene-2-carboxylic acid.

In a similar manner when the halomethylated derivative and the isothiourea derivative listed in the following Table X are reacted as in Example 28(A) and the resulting product subsequently treated as in Example 28(B) the respective products listed in Table X are obtained.

TABLE X

| Halomethylated Derivative | Isothiourea Derivative | Product |
| --- | --- | --- |
| 6-[[2-[4-(chloromethyl)phenyl]-2-aminoacetyl]amino]-3,3-dimethyl-7-oxo-4-thia-1-azabicyclo[3.2.0]-heptane-2-carboxylic acid | n-propylisothiourea | 6-[[2-[4-(n-propylisothioureamethyl)-phenyl]-2-aminoacetyl]amino]-3,3-dimethyl-7-oxo-4-thia-1-azabicyclo-[3.2.0]heptane-2-carboxylic acid |
| 3-[(acetyloxy)methyl]-7-[[3-[4-(chloromethyl)phenyl]-2-aminopropionyl]amino]-8-oxo-5-thia-1-azabicyclo[4.2.0]oct-2-ene-2-carboxylic acid | 1-ethyl-3-methylisothiourea | 3-[(acetyloxy)methyl]-7-[[3-[4-(1-ethyl-3-methylisothioureamethyl)-phenyl]-2-aminopropionyl]amino]-8-oxo-5-thia-1-azabicyclo[4.2.0]oct-2-ene-2-carboxylic acid |
| 3-[(acetyloxy)methyl]-7-[[4-[4-(chloromethyl)phenoxy]-2-aminobutyryl]amino]-8-oxo-5-thia-1-azabicyclo[4.2.0]oct-2-ene-2-carboxylic acid | isothiourea | 3-[(acetyloxy)methyl]-7-[[4-[4-(isothioureamethyl)phenoxy]-2-aminobutyryl]amino]-8-oxo-5-thia-1-azabicyclo[4.2.0]-oct-2-ene-2-carboxylic acid |
| 3-[(acetyloxy)methyl]-7-[[4-[4-(chloromethyl)anilino]-2-aminobutyryl]amino]-8-oxo-5-thia-1-azabicyclo[4.2.0]oct-2-ene-2-carboxylic acid | isothiourea | 3-[(acetyloxy)methyl]-7-[[4-[4-(isothioureamethyl)anilino]-2-aminobutyryl]amino]-8-oxo-5-thia-1-azabicyclo[4.2.0]oct-2-ene-2-carboxylic acid |
| 3-[(acetyloxy)methyl]-7-[[3-[4-(chloromethyl)phenylthio]-2-aminopropionyl]amino]-8-oxo-5-thia-1-azabicyclo[4.2.0]oct-2-ene-2-carboxylic acid | isothiourea | 3-[(acetyloxy)methyl]-7-[[3-[4-(isothioureamethyl)phenylthio]-2-aminopropionyl]amino]-8-oxo-5-thia-1-azabicyclo[4.2.0]oct-2-ene-2-carboxylic acid |
| 3-[(acetyloxy)methyl]-7-[[2-(5-(chloromethyl)-2-thienyl]-2-aminoacetyl]amino]-8-oxo-5-thia-1-azabicyclo[4.2.0]oct-2-ene-2-carboxylic acid | 1,3-di-n-propylisothiourea | 3-[(acetyloxy)methyl)-7-[[2-[5-(1,3-di-n-propylisothioureamethyl)-2-thienyl]-2-aminoacetyl]amino]-8-oxo-5-thia-1-azabicyclo[4.2.0]oct-2-ene-2-carboxylic acid |
| 3-[(acetyloxy)methyl]-7-[[4-[5-(chloromethyl)-2-thienyl]-2-aminobutyryl]amino]-8-oxo-5-thia-1-azabicyclo[4.2.0]oct-2-ene-2-carboxylic acid | 1-ethylisothiourea | 3-[(acetyloxy)methyl]-7-[[4-[5-(1-ethylisothioureamethyl)-2-thienyl]-2-aminobutyryl]amino]-8-oxo-5-thia-1-azabicyclo[4.2.0]oct-2-ene-2-carboxylic acid |
| 6-[[3-[4-(chloromethyl)phenyl]-2-aminopropionyl]amino]-3,3-dimethyl-7-oxo-4-thia-1-azabicyclo-[3.2.0]heptane-2-carboxylic acid | isothiourea | 6-[[3-[4-(isothioureamethyl)phenyl]-2-aminopropionyl]amino]-3,3-dimethyl-7-oxo-4-thia-1-azabicyclo[3.2.0]heptane-2-carboxylic acid |
| 6-[[4-[4-(chloromethyl)phenoxy]-2-aminobutyryl]amino]-3,3-dimethyl-7-oxo-4-thia-1-azabicyclo[3.2.0]-heptane-2-carboxylic acid | isothiourea | 6-[[4-[4-(isothioureamethyl)phenoxy]-2-aminobutyryl]amino]-3,3-dimethyl-7-oxo-4-thia-1-azabicyclo[3.2.0]heptane-2-carboxylic acid |
| 6-[[4-[4-(chloromethyl)anilino]-2-aminobutyryl]amino-3,3-dimethyl-7-oxo-4-thia-1-azabicyclo[3.2.0]-heptane-2-carboxylic acid | 1,3-diethylisothiourea | 6-[[4-[4-(1,3-diethylisothioureamethyl)anilino]-2-aminobutyryl]-amino-3,3-dimethyl-7-oxo-4-thia-1-azabicyclo[3.2.0]heptane-2-carboxylic acid |
| 6-[[3-[4-(chloromethyl)phenylthio]-2-aminopropionyl]amino]-3,3-dimethyl-7-oxo-4-thia-1-azabicyclo-[3.2.0]heptane-2-carboxylic acid | 1,1-dimethyl-3-ethylisothiourea | 6-[[3-[4-(1,1-dimethyl-3-ethylisothioureamethyl)phenylthio]-2-aminopropionyl]amino] -3,3-dimethyl-7-oxo-4-thia-1-azabicyclo[3.2.0]heptane-2-carboxylic acid |
| 6-[[2-[5-(chloromethyl)-2-thienyl]-2-aminoacetyl]amino]-3,3,-dimethyl-7-oxo-4-thia-1-azabicyclo[3.2.0]-heptane-2-carboxylic acid | isothiourea | 6-[[2-[5-(isothioureamethyl)-2-thienyl]-2-aminoacetyl]amino]-3,3-dimethyl-7-oxo-4-thia-1-azabicyclo[3.2.0]-heptane-2-carboxylic acid |
| 3-(2-methyl-1,3,4-thiadiazol-5-yl-thio)-7-[[2-[4-(chloromethyl)phenyl]-2-aminoacetyl]amino]-8-oxo-5-thia-1-azabicyclo[4.2.0]oct-2-ene-2-carboxylic acid | isothiourea | 3-(2-methyl-1,3,4-thiadiazol-5-ylthio)-7-[[2-[4-(isothioureamethyl)phenyl]-2-aminoacetyl]amino]-8-oxo-5-thia-1-azabicyclo[4.2.0]oct-2-ene-2-carboxylic acid |

TABLE X-continued

| Halomethylated Derivative | Isothiourea Derivative | Product |
| --- | --- | --- |
| 3-[(acetyloxy)methyl]-7-[[2-[4-(chloromethyl)phenyl]-2-aminoacetyl]amino]-8-oxo-5-thia-1-azabicyclo[4.2.0]oct-2-ene-2-carboxylic acid pivalyloxymethyl ester | isothiourea | 3-[(acetyloxy)methyl]-7-[[2-[4-(isothioureamethyl)phenyl]-2-aminoacetyl]amino]-8-oxo-5-thia-1-azabicyclo[4.2.0]oct-2-ene-2-carboxylic acid pivalyloxymethyl ester |
| 3-(1-methyltetrazol-5-ylthio)-7-[[2-[4-(chloromethyl)phenyl]-2-aminoacetyl]amino]-8-oxo-5-thia-1-azabicyclo[4.2.0]oct-2-ene-2-carboxylic acid | isothiourea | 3-(1-methyltetrazol-5-ylthio)-7-[[2-[4-(isothioureamethyl)phenyl]-2-aminoacetyl]amino]-8-oxo-5-thia-1-azabicyclo[4.2.0]oct-2-ene-2-carboxylic acid |

EXAMPLE 29

3-[(Acetyloxy)methyl]-7-[[2-[4-(isothioureamethyl)-phenyl]-acetyl]amino]-8-oxo-5-thia-1-azabicyclo[4.2.0]oct-2-ene-2-carboxylic acid -N-ethoxycarbonyl-N-methylaminomethyl ester A mixture of 1.2 g of the sodium salt of 3-[(acetyloxy)methyl]-7-[[2-[4-(isothioureamethyl)phenyl]acetyl]-amino]-8-oxo-5-thia-1-azabicyclo[4.2.0]oct-2-ene-2-carboxylic acid and 0.5 g of N-chloromethyl-N-methylurethane in 40 ml of dimethylformamide is stirred at room temperature for 2 hours. The mixture is poured into ice-water and decanted. The oily residue is taken up in 75 ml of ethyl acetate and washed with 5 ml of dilute aqueous sodium bicarbonate and 15 ml of water then dried over magnesium sulfate, filtered and evaporated to give 3-[(acetyloxy)methyl]-7-[[2-[4-(isothioureamethyl)phenyl]acetyl]amino]-8-oxo-5-thia-1-azabicyclo[4.2.0]oct-2-ene-2-carboxylic acid N-ethoxycarbonyl-N-methylaminomethyl ester.

EXAMPLE 30

3-[(Acetyloxy)methyl]-7-[[2-[4-(isothioureamethyl)-phenyl]acetyl]amino]-8-oxo-5-thia-1-azabicyclo[4.2.0]-oct-2-ene-2-carboxylic acid-p-pivalyoxybenzyl ester To a solution of 1.8 g of 3-[(acetyloxy)methyl]-7-[[2-[4-(isothioureamethyl)phenyl]acetyl]amino]-8-oxo-5-thia-1-azabicyclo[4.2.0]oct-2-ene-2-carboxylic acid hydrochloride in 25 ml of dimethyl formamide is added 0.78 g of p-pivalyoxybenzyl alcohol followed by cooling to 0° C after which 3.7 mole of dicyclohexylcarbodiimide in 7.5 ml of dimethyl formamide is added dripwise with stirring. The reaction mixture is stirred for 1 hour at 0° C and for an additional 4 hours at room temperature. The formed dicyclohexylurea is removed by filtration. The filtrate is diluted with chloroform and washed with water. The organic layer is then dried over magnesium sulfate filtered and evaporated in vacuo to give an oil which is triturated with ether to give 3-[(acetyloxy)methyl]-7-[[2-[4-(isothioureamethyl)-phenyl]acetyl]amino]-8-oxo-5-thia-1-azabicyclo[4.2.0]oct-2-ene-2-carboxylic acid p-pivalyloxybenzyl ester.

EXAMPLE 31

A. When in the procedure of Example 14 an appropriate amount of 3-(acetyloxy]methyl]-7-amino-7-methoxy-8-oxo-5-thia-1-azabicyclo[4.2.0]oct-2-ene-2-carboxylic acid, prepared by acid hydrolysis of the corresponding benzhydryl ester described in U.S. Pat. No. 3,778,432, or the corresponding 3-(2-methyl-1,3,4-thiadiazol-5-ylthio derivative is substituted for 3-[(acetyloxy)-methyl]-7-amino-8-oxo-5-thia-1-azabicyclo[4.2.0]oct-2-ene-2-carboxylic acid, 3-[(acetyloxy)methyl]-7-[[2-[4-(chloromethyl)phenyl]acetyl]amino]-7-methoxy-8-oxo-5-thia-1-azabicyclo[4.2.0]oct-2-ene-2-carboxylic acid and the corresponding 3-(2-methyl-1,3,4-thiadiazol-5-ylthio derivative are obtained respectively.

B. When in the procedure of Example 27 appropriate amounts of each of the above obtained 7-methoxy derivatives are substituted for 3-[(acetyloxy)methyl]-7-[[2-[4-(chloromethyl)phenyl]acetyl]amino]-8-oxo-5-thia-1-azabicyclo-[4.2.0]oct-2-ene-2-carboxylic acid, 3-[(acetyloxy)methyl]-7-[[2-[4-(isothioureamethyl)phenyl]acetyl]amino]-7-methoxy-8-oxo-5-thia-1-azabicyclo[4.2.0]oct-2-ene-2-carboxylic acid and 3-(2-methyl-1,3,4-thiadiazol-5-ylthio)-7-[[2-[4-(isothioureamethyl)phenyl]acetyl]amino]-7-methoxy-8-oxo-5-thia-1-azabicyclo]4.2.0]oct-2-ene-2-carboxylic acid are obtained.

EXAMPLE 32

3-](Acetyloxy)methyl]-7-[[2-[4-(isothioureamethyl)-phenyl]-2-(5-indanyloxycarbonyl)acetyl]amino]-8-oxo-5-thia-1-azabicyclo[4.2.0 oct-2-ene-2-carboxylic acid To 25.3 m mole of the cephalosporin in 35 ml dioxane is added 6N hydrochloric acid to give a pH of 2.5. Then 24.1 m moles N,N'-dicyclohexylcarbodiimide in 35 ml dioxane is added and the mixture is stirred at room temperature for 15 to 20 minutes followed by the addition of 24.1 m moles of 5-indanol. The mixture is stirred for 4 hours. The formed N,N'-dicyclohexylurea is removed by filtration and the filtrate is extracted three times with methyl isobutyl ketone. The organic extract is washed with water, dried over magnesium sulfate and concentrated to dryness in vacuo to yield 3-[(acetyloxy)methyl]-7-[[2-[4-(isothioureamethyl]-phenyl]-2-(5-indanyloxycarbonyl)acetyl]amino]-8-oxo-5-thia-1-azabicyclo[4.2.0]oct -2-ene-2-carboxylic acid.

EXAMPLE 33 o-Isothioureamethylphenylacetic acid hydrochloride

A solution of 0.25 g (1.33 mM) of p-chlorophenylacetic acid and 0.25 g (3.33 mM) of isothiourea is refluxed in 65 ml of ethanol for 3½ hours after which the solvent is removed in vacuo at room temperature. The resulting oil is triturated with 110 ml of acetone/benzene (1:2) to give p-isothioureamethylphenylacetic acid hydrochloride as a white solid, M.P. 173°–175° C.

In a similar manner when appropriate amounts of the acid derivatives and isothiourea derivatives listed below in Table XI are substituted respectively for p-chlorophenylacetic acid and isothiourea in the above procedure the respective products listed in Table XI are obtained.

TABLE XI

| Acid | Isothiourea Derivative | Product |
|---|---|---|
| p-chloromethyl-2-methylhydro-cinnamic acid | isothiourea | p-isothioureamethyl-2-methylhydro-cinnamic acid hydrochloride |
| 3-(p-chloromethylphenyl)lactic acid | isothiourea | 3-(p-isothioureamethylphenyl)lactic acid hydrochloride |
| 4-(p-chloromethylphenyl)butyric acid | n-propylisothiourea | 4-(p-n-propylisothioureamethylphenyl)-butyric acid hydrochloride |
| p-chloromethylphenoxyacetic acid | isothiourea | p-isothioureamethylphenoxyacetic acid hydrochloride |
| 2-(p-chloromethylphenoxy)propionic acid | 1,1-diethyl-3-methyl-isothiourea | 2-[p-(1,1-diethyl-3-methylisothiourea-methyl)phenoxy]propionic acid hydrochloride |
| 4-(p-chloromethylphenoxy)butyric acid | isothiourea | 4-(p-isothioureamethylphenoxy)butyric acid hydrochloride |
| 2-(p-chloromethylanilino)propionic acid | isothiourea | 2-(p-isothioureamethylanilino)propionic acid hydrochloride |
| 4-(p-chloromethylanilino)butyric acid | n-propylisothiourea | 4-(p-n-propylisothioureamethylanilino)-butyric acid hydrochloride |
| p-chloromethylphenylthioacetic acid | 1-ethyl-3-methyl-isothiourea | p-(1-ethyl-3-methylisothioureamethyl)-phenylthioacetic acid hydrochloride |
| 2-amino-4-(p-chloromethylphenyl)-butyric acid | isothiourea | 2-amino-4-(p-isothioureamethylphenyl)-butyric acid hydrochloride |
| 2-amino-4-(p-chloromethylphenoxy)-butyric acid | isothiourea | 2-amino-4-(p-isothioureamethylphenoxy)-butyric acid hydrochloride |
| 2-amino-4-(p-chloromethylanilino)-butyric acid | isothiourea | 2-amino-4-(p-isothioureamethylanilino)-butyric acid hydrochloride |
| 2-sulfo-p-chloromethylphenylacetic acid | 1,1-diethylisothiourea | 2-sulfo-p-(1,1-diethylisothioureamethyl)phenylacetic acid hydrochloride |
| p-chloromethylphenylmalonic acid | isothiourea | p-isothioureamethylphenylmalonic acid hydrochloride |
| 2-(p-chloromethylphenoxy)ethyl-malonic acid | n-propylisothiourea | 2-(p-n-propylisothioureamethylphenoxy)-ethylmalonic acid hydrochloride |
| p-chloromethylanilinomethylmalonic acid | isothiourea | p-isothioureamethylanilinomethyl-malonic acid hydrochloride |

EXAMPLE 34

3-[(Acetyloxy)methyl]-7-[[2-[4-(isothioureamethyl)-phenyl]-acetyl]amino]-8-oxo-5-thia-1-azabicyclo[4.2.0]oct-2-ene-2-carboxylic acid A mixture of 1.2 grams of 3-[(acetyloxy)methyl]-7-amino-8-oxo-5-thia-1-azabicyclo[4.2.0]oct-2-ene-2-carboxylic acid and 1.2 grams of p-isothioureamethylphenylacetic acid chloride HCl in 55 ml of ethyl acetate is refluxed for 1½ hours after which the solvent is removed yielding 3-[(acetyloxy)methyl]-7-[[2-[4-(isothioureamethyl)phenyl]-acetyl]amino]-8-oxo-5-thia-1-azabicyclo[4.2.0]oct-2-ene-2-carboxylic acid which can be further purified by column chromatography.

Similarly when an appropriate amount of 6-amino-3,3-dimethyl-7-oxo-4-thia-1-azabicyclo[3.2.0]heptane-2-carboxylic acid is substituted for 3-[(acetyloxy)methyl]-7-amino-8-oxo-5-thia-1-azabicyclo[4.2.0]oct-2-ene-2-carboxylic acid in the above procedure, 6-[[2-[4-(isothioureamethyl)phenyl]acetyl]amino]-3,3-dimethyl-7-oxo-4-thia-1-azabicyclo[3.2.0]heptane-2-carboxylic acid is obtained.

When in the above described procedure appropriate amounts of the cephalosporin derivative and the isothiourea derivative as the acid chloride hydrochloride listed below in Table XII are substituted respectively for 3-[(acetyloxy)-methyl]-7-amino-8-oxo-5-thia-1-azabicyclo[4.2.0]oct-2-ene-2-carboxylic acid and p-isothioureamethylphenylacetic acid the respective products in Table XII are obtained.

TABLE XII

| Cephalosporin Derivative | Isothiourea Derivative | Product |
|---|---|---|
| 3-[(acetyloxy)methyl]-7-amino-8-oxo-5-thia-1-azabicyclo[4.2.0]oct-2-ene-2-carboxylic acid propionyloxymethyl ester | p-isothioureamethyl-2-methylhydrocinnamic acid | 3-[(acetyloxy)methyl]-7-[[3-[4-isothioureamethyl)phenyl]-2-methylpropionyl]amino]-8-oxo-5-thia-1-azabicyclo[4.2.0]oct-2-ene-2-carboxylic acid propionyloxymethyl ester |
| 3-[(acetyloxy)methyl]-7-amino-8-oxo-5-thia-1-azabicyclo[4.2.0]oct-2-ene-2-carboxylic acid pivalyloxymethyl ester | 4-(p-n-propylisothio-ureamethylphenyl)butyric acid | 3-[(acetyloxy)methyl]-7-[[4-[4-(n-propylisothioureamethyl)phenyl]butyryl]-amino]-8-oxo-5-thia-1-azabicyclo[4.2.0]-oct-2-ene-2-carboxylic acid pivalyloxymethyl ester |
| 3-[(acetyloxy)methyl]-7-amino-8-oxo-5-thia-1-azabicyclo[4.2.0]oct-2-ene-2-carboxylic acid pivalyloxybenzyl ester | p-isothioureamethyl-phenoxyacetic acid | 3-[(acetyloxy)methyl]-7-[[2-[4-(p-isothioureamethyl)phenoxy]acetyl]amino]-8-oxo-5-thia-1-azabicyclo[4.2.0]oct-2-ene-2-carboxylic acid pivalyloxybenzyl ester |
| 3-[(acetyloxy)methyl]-7-amino-8-oxo-5-thia-1-azabicyclo[4.2.0]oct-2-ene-2-carboxylic acid 2-amino-3-methylbutyryloxymethyl ester | 2-[p-(1,1-diethyl-3-methylisothioureamethyl)-phenoxy]propionic acid | 3-[(acetyloxy)methyl]-7-[[3-[4-(1,1-diethyl-3-methylisothioureamethyl)-phenoxy]propionyl]amino]-8-oxo-5-thia-1-azabicyclo[4.2.0]oct-2-ene-2-carboxylic acid 2-amino-3-methylbutyryloxymethyl ester |
| 3-[(acetyloxy)methyl]-7-amino-8-oxo 5-thia-1-azabicyclo[4.2.0]oct-2-ene-carboxylic acid N-ethoxycarbonyl-N-methylaminomethyl ester | 4-(p-isothioureamethyl-phenoxy)butyric acid | 3-[(acetyloxy)methyl]-7-[[4-[4-(isothioureamethyl)phenoxy]butyryl]amino]-8-oxo-5-thia-1-azabicyclo[4.2.0]oct-2-ene-2-carboxylic acid N-ethoxycarbonyl-N-methylaminomethyl ester |
| 3-(2-methyl-1,3,4-thiadiazol-5-yl-thio)-7-amino-8-oxo-5-thia-1-azabi- | 2-(p-isothioureamethyl)-anilinopropionic acid | 3-(2-methyl-1,3,4-thiadiazol-5-ylthio)-7-[[3-[4-(isothioureamethyl)anilino]- |

TABLE XII-continued

| Cephalosporin Derivative | Isothiourea Derivative | Product |
|---|---|---|
| cyclo[4.2.0]oct-2-ene-2-carboxylic acid | | propionyl]amino]-8-oxo-5-thia-1-azabicyclo[4.2.0]oct-2-ene-2-carboxylic acid |
| 3-(1-methyltetrazol-5-ylthio)-7-amino-8-oxo-5-thia-1-azabicyclo-[4.2.0]oct-2-ene-2-carboxylic acid | 4-(p-n-propylisothioureamethylanilino]-butyric acid | 3-(1-methyltetrazol-5-ylthio)-7-[[4-[4-n-propylisothioureamethyl)anilino]-butyryl]amino]-8-oxo-5-thia-1-azabicyclo[4.2.0]oct-2-ene-2-carboxylic acid |
| 3-[(acetyloxy)methyl]-7-amino-8-oxo-5-thia-1-azabicyclo[4.2.0]-oct-2-ene-2-carboxylic acid | p-(1-ethyl-3-methylisothioureamethyl)phenylthioacetic acid | 3-[(acetyloxy)methyl]-7-[[2-[4-(1-ethyl-3-methylisothioureamethyl)phenylthio]acetyl]amino]-8-oxo-5-thia-1-azabicyclo[4.2.0]oct-2-ene-2-carboxylic acid |
| 3-(3-methyl-1,3,4-thiadiazol-5-ylthio)-7-amino-8-oxo-5-thia-1-azabicyclo[4.2.0]oct-2-ene-2-carboxylic acid pivalyloxymethyl ester | *2-amino-4-(p-isothioureamethylphenyl)butyric acid | 3-(3-methyl-1,3,4-thiadiazol-5-ylthio)-7-[[4-[4-(isothioureamethyl)phenyl]2-aminobutyryl]amino]-8-oxo-5-thia-1-azabicyclo[4.2.0]oct-2-ene-2-carboxylic acid pivalyloxymethyl ester |
| 3-[(acetyloxy)methyl]-7-amino-8-oxo-5-thia-1-azabicyclo[4.2.0]-oct-2-ene-2-carboxylic acid | *2-amino-4-(p-isothioureamethylphenoxy)-butyric acid | 3-[(acetyloxy)methyl]-7-[[4-[4-(isothioureamethyl)phenoxy]-2-aminobutyryl]amino]-8-oxo-5-thia-1-azabicyclo[4.2.0]-oct-2-ene-2-carboxylic acid. |

*The amino group is protected by a suitable blocking group, such as tert-butoxycarbonyl, prior to coupling and the protecting group is removed from the reaction product by procedures known in the art.

EXAMPLE 35

3-(2-Methyl-1,3,4-thiadiazol-5-ylthio)-7-[[2-[4-(isothioureamethyl)phenyl]acetyl]amino]-8-oxo-5-thia-1-azabicyclo[4.2.0]oct-2-ene-2-carboxylic acid A solution of 3 mM of 3-[(acetyloxy)-methyl]-7-[[2-[4-(isothioureamethyl)phenyl]acetyl]amino]-8-oxo-5-thia-1-azabicyclo[4.2.0]oct-2-ene-2-carboxylic acid in 100 ml of water is treated with 3 mM of sodium bicarbonate and 6 mM of 2-methyl-1,3,4-thiadiazol-5-ylthio at 70° C under nitrogen for 3½ hours. The water is removed in vacuo and the residue is taken up in methanol. A large excess of acetonitrile is added to precipitate the product which is isolated by filtration and dried in a vacuum desiccator to give 3-(2-methyl-1,3,4-thiadiazol-5-ylthio)-7-[[2-[4-(isothioureamethyl)phenyl]acetyl]amino]-8-oxo-5-thia-1-azabicyclo[4.2.0]oct-2-ene-2-carboxylic acid.

When appropriate amounts of the cephalosporin derivatives and the thiol derivatives listed below in Table XIII are substituted for the cephalosporin derivative and thiol derivative in the above procedure the respective products listed in Table XIII are obtained:

TABLE XIII

| Cephalosporin Derivative | Thiol Derivative | Product |
|---|---|---|
| 3-[(acetyloxy)methyl]-7-[[3-[4-(isothioureamethyl)phenylthio]-2-aminopropionyl]amino]-8-oxo-5-thia-1-azabicyclo[4.2.0]oct-2-ene-2-carboxylic acid | 1-methyltetrazol-5-ylthiol | 3-(1-methyltetrazol-5-ylthio)-7-[[3-[4-(isothioureamethyl)phenylthio]-2-aminopropionyl]amino]-8-oxo-5-thia-1-azabicyclo[4.2.0]oct-2-ene-2-carboxylic acid |
| 3-[(acetyloxy)methyl]-7-[[3-[4-(1,3-di-n-propylisothioureamethyl)anilino]-2-carboxypropionyl]amino]-8-oxo-5-thia-1-azabicyclo[4.2.0]oct-2-ene-2-carboxylic acid | 2-methyl-1,3,4-thiadiazol-5-ylthiol | 3-(2-methyl-1,3,4-thiadiazol-5-ylthio)-7-[[3-[4-(1,3-di-n-propylisothioureamethyl)anilino]-2-carboxypropionyl]amino]-8-oxo-5-thia-1-azabicyclo[4.2.0]oct-2-ene-2-carboxylic acid |
| 3-[(acetyloxy)methyl]-7-[[2-[4-(1-methyl-3-ethylisothioureamethyl)-phenyl]-2-sulfoacetyl]amino]-8-oxo-5-thia-1-azabicyclo[4.2.0]oct-2-ene-2-carboxylic acid | 3-methyl-1,2,4-thiadiazol-5-ylthio | 3-(3-methyl-1,2,4-thiadiazol-5-ylthio)-7-[[2-[4-(1-methyl-3-ethylisothioureamethyl)phenyl]-2-sulfoacetyl]amino]-8-oxo-5-thia-1-azabicyclo[4.2.0]oct-2-ene-2-carboxylic acid |
| 3-[(acetyloxy)methyl]-7-[[3-[4-(1,3-diethylisothioureamethyl)phenyl]-2-hydroxypropionyl]amino]-8-oxo-5-thia-1-azabicyclo[4.2.0]oct-2-ene-2-carboxylic acid | tetrazol-5-ylthiol | 3-(tetrazol-5-ylthio)-7-[[3-[4-(1,3-diethylisothioureamethyl)phenyl]-2-hydroxypropionyl]amino]-8-oxo-5-thia-1-azabicyclo[4.2.0]oct-2-ene-2-carboxylic acid |
| 3-[(acetyloxy)methyl]-7-[[3-[4-(isothioureamethyl)anilino]-2-methylpropionyl]amino]-8-oxo-5-thia-1-azabicyclo[4.2.0]oct-2-ene-2-carboxylic acid | 2-methyl-1,3,4-oxadiazol-5-ylthiol | 3-(2-methyl-1,3,4-oxadiazol-5-ylthio)-7-[[3-[4-(isothioureamethyl)anilino]-2-methylpropionyl]amino]-8-oxo-5-thia-1-azabicyclo[4.2.0]oct-2-ene-2-carboxylic acid |
| 3-[(acetyloxy)methyl]-7-[[2-[4-(isothioureamethyl)phenoxy]acetyl]amino]-8-oxo-5-thia-1-azabicyclo[4.2.0]-oct-2-ene-2-carboxylic acid | 2-methyl-1,3,4-thiadiazol 5-ylthiol | 3-(2-methyl-1,3,4-thiadiazol-5-ylthio)-7-[[2-[4-(isothioureamethyl)phenoxy]acetyl]amino]-8-oxo-5-thia-1-azabicyclo[4.2.0]oct-2-ene-2-carboxylic acid |
| 3-[(acetyloxy)methyl]-7-[[2-[4-(1,1-diethyl-3-methylisothioureamethyl)-phenyl]-2-methylacetyl]amino]-8-oxo-5-thia-1-azabicyclo[4.2.0]oct-2-ene-2-carboxylic acid | 1-methyltetrazol-5-ylthiol | 3-(1-methyltetrazol-5-ylthio)-7-[[2-[4-(1,1-diethyl-3-methylisothioureamethyl)phenyl]-2-methylacetyl]amino]-8-oxo-5-thia-1-azabicyclo[4.2.0]oct-2-ene-2-carboxylic acid |
| 3-[(acetyloxy)methyl]-7-[[2-[4-(isothioureamethyl)phenyl]-2-carboxyacetyl]amino]-8-oxo-5-thia-1-azabicyclo[4.2.0]oct-2-ene-2-carboxylic | 2-methyl-1,3,4-thiadiazol-5-ylthiol | 3-(2-methyl-1,3,4-thiadiazol-5-ylthio)-7-[[2-[4-(isothioureamethyl)phenyl]-2-carboxyacetyl]amino]-8-oxo-5-thia-1-azabicyclo[4.2.0]oct- |

TABLE XIII-continued

| Cephalosporin Derivative | Thiol Derivative | Product |
|---|---|---|
| acid | | 2-ene-2-carboxylic acid |

EXAMPLE 36

When in the procedure of Example 14 appropriate amounts of 3-(2-methyl-1,3,4-thiadiazol-5-ylthio)-7-amino-8-oxo-5-thia-1-azabicyclo[4.2.0]oct-2-ene-2-carboxylic acid or 3-(1-methyltetrazol-5-ylthio)-7-amino-8-oxo5-thia-1-azabicyclo[4.2.0]oct-2-ene-2-carboxylic acid are substituted for 3-acetyloxymethyl-7-amino-8-oxo-5-thia-1-azabicyclo[4.2.0]oct-2-ene-2-carboxylic acid and 2-sulfo-p-chloromethylphenylacetyl chloride prepared from the corresponding acid is substituted for p-chloromethylphenylacetyl chloride the following respective products are obtained. 3-(2-methyl-1,3,4-thiadiazol-5-ylthio)-7-[[2-[4-(chloromethyl)phenyl]-2-sulfoacetyl]amino]-8-oxo-5-thia-1-azabicyclo[4.2.0]oct-2-ene-2-carboxylic acid and 3-(1-methyltetrazol-5-ylthio)-7-[[2-[4-(chloromethyl)-phenyl]-2-sulfoacetyl]amino]-8-oxo-5-thia-1-azabicyclo[4.2.0]oct-2-ene-2-carboxylic acid.

When in the procedure of Example 27 an appropriate amount of each of the above obtained chloromethyl substituted cephalosporin derivatives is substituted for 3-[(acetyloxy)methyl]-7-[[2-[4-(chloromethyl)-phenyl]acetyl]amino]-8-oxo-5-thia-1-azabicyclo[4.2.-0]oct-2-ene-2-carboxylic acid the following respective products are obtained:

3-(2-methyl-1,3,4-thiadiazol-5-ylthio)-7-[[2-[4-isothioureamethyl)phenyl]-2-sulfoacetyl]amino]-8-oxo-5-thia-1-azabicyclo[4.2.0]oct-2-ene-2-carboxylic acid and 3-(1-methyltetrazol-5-ylthio)-7-[[2-[4-(isothioureamethyl)-phenyl]-2-sulfoacetyl]amino]-8-oxo-5-thia-1-azabicyclo-[4.2.0]oct-2-ene-2-carboxylic acid.

We claim:

1. A compound selected from a base of the formula

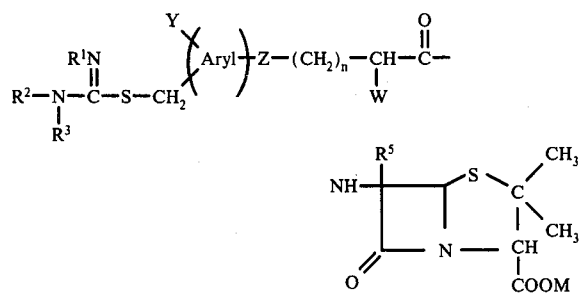

wherein Aryl is selected from phenyl or 2-thienyl; Y is selected from hydrogen, chlorine, bromine, a straight or branched lower alkyl group of from 1 to 4 carbon atoms, or an alkoxy group of from 1 to 4 carbon atoms with the proviso that when Aryl is 2-thienyl, Y is hydrogen; each of $R^1$, $R^2$ and $R^3$ is selected from hydrogen or a straight or branched lower alkyl group of from 1 to 4 carbon atoms; Z is selected from a bond, oxygen, sulfur or imino with the proviso that when Aryl is 2-thienyl, Z is a bond; W is selected from hydrogen, methyl, anino, hydroxy, $SO_3H$, or $COOR^4$ wherein $R^4$ is selected from hydrogen or 5-indanyl; n is zero, 1 or 2 with the proviso that when W is other than hydrogen or methyl and Z is other than a bond, n is not zero; $R^5$ is selected from hydrogen or methoxy; M is selected from hydrogen, a pharmaceutically acceptable non-toxic cation charge, an alkanoyloxymethyl group wherein the alkanoyl moiety has from 1 to 5 carbon atoms and may be straight or branched, an alkanoylaminomethyl group wherein the alkanoyl moiety has from 1 to 5 carbon atoms and may be straight or branched and wherein the amino nitrogen may be substituted with an alkyl group of from 1 to 4 carbon atoms, an alkoxycarbonylaminomethyl group wherein the alkoxy moiety has from 1 to 4 carbon atoms and may be straight or branched and wherein the amino nitrogen may be substituted with an alkyl group of from 1 to 4 carbon atoms, p-(alkanoyloxy)benzyl wherein the alkanoyl moiety contains from 1 to 5 carbon atoms and may be straight or branched or aminoalkanoyloxymethyl as represented by the group

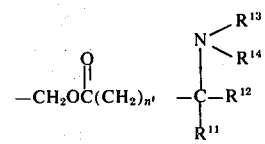

wherein $n'$ is 0 to 5, each of $R^{11}$ and $R^{12}$ is selected from hydrogen or lower alkyl of from 1 to 4 carbon atoms, and each of $R^{13}$ and $R^{14}$ is selected from hydrogen or a straight or branched lower alkyl group of from 1 to 4 carbon atoms; and pharmaceutically acceptable salts thereof.

2. A compound of claim 1 wherein W is hydrogen.
3. A compound of claim 2 wherein Z is a bond.
4. A compound of claim 2 wherein Z is oxygen or sulfur.
5. A compound of claim 2 wherein Z is imino.
6. A compound of claim 1 wherein W is methyl.
7. A compound of claim 6 wherein Z is a bond.
8. A compound of claim 6 wherein Z is oxygen or sulfur.
9. A compound of claim 6 wherein Z is imino.
10. A compound of claim 1 wherein W is hydroxy.
11. A compound of claim 10 wherein Z is a bond.
12. A compound of claim 10 wherein Z is oxygen or sulfur.
13. A compound of claim 10 wherein Z is imino.
14. A compound of claim 1 wherein W is amino.
15. A compound of claim 14 wherein Z is a bond.
16. A compound of claim 14 wherein Z is oxygen or sulfur.
17. A compound of claim 14 wherein Z is imino.
18. A compound of claim 1 wherein W is $COOR^4$ or $SO_3H$.
19. A compound of claim 18 wherein Z is a bond.
20. A compound of claim 18 wherein Z is oxygen or sulfur.
21. A compound of claim 18 wherein Z is imino.

* * * * *

UNITED STATES PATENT AND TRADEMARK OFFICE
CERTIFICATE OF CORRECTION

PATENT NO. : 3,994,875
DATED : November 30, 1976
INVENTOR(S) : F. Haviv and A. Patchornik It is certified that error appears in the above-identified patent and that said Letters Patent are hereby corrected as shown below:

Column 1, line 9 "peparation" should read "preparation".

Column 3, line 55 "$(CH_2)_n\overset{O}{\underset{\|}{C}}-NH-$" should read "$(CH_2)_n-\underset{\underset{W}{|}}{CH}-\overset{O}{\underset{\|}{C}}-NH-$".

Column 6, line 36-37 "-51-ylthio" should read "-5-ylthio".
Column 12, line 5 "cephalosporin in derivatives" should read "cephalosporin derivatives". Column 13, line 16 "$W^a$" should read "$W^2$". Column 21, line 66 "ppivalyloxybenzyl" should read "p-pivalyloxybenzyl". Column 30, line 63 "-(chloromethyl]-2-" should read "-(chloromethyl]phenylthio]-2-". Column 31, line 9 "acic" should read "acid". Column 31, line 43 "amountof of" should read "amount of". Table IX, 5th listing, 1st column "-5-ylthio)-7-" should read "-5-ylthio)methyl]-7-"; Table IX, 5th listing, 1st column "-azibicyclo" should read "-azabicyclo"; Table IX, 5th listing, 3rd column "-5-ylthio)-7-" should read "-5-ylthio)methyl]-7-"; Table IX, 6th listing, 1st column "-5-ylthio)-7-" should read "-5-ylthio)methyl]-7-"; Table IX, 6th listing, 3rd column "-5-ylthio)-7-" should read "-5-ylthio)methyl]-7-"; Table IX, 7th listing, 1st column "-5-ylthio)-7-" should read "-5-ylthio)methyl]-7-"; Table IX, 7th listing, 3rd column "-5-ylthio)-7-" should read "-5-ylthio)methyl]-7-"; Table IX 31st listing, 1st column "-5-ylthio]-7-" should read "-5-ylthio)methyl]-7-"; Table IX, 56th listing, 1st column "-5-ylthio)-7-" should read "-5-ylthio)methyl]-7-"; Table IX, 56th listing, 3rd column "-5-ylthio)-7-" should read "-5-ylthio)methyl]-7-"; Table IX, 57th listing, 1st column "-5-ylthio)-7-" should read "-5-ylthio)methyl]-7-"; Table IX, 57th listing, 3rd column "-5-ylthio)-7-" should read "-5-ylthio)methyl]-7-"; Table IX, 59th listing, 1st column "-5-

UNITED STATES PATENT AND TRADEMARK OFFICE
CERTIFICATE OF CORRECTION

PATENT NO. : 3,994,875
DATED : November 30, 1976
INVENTOR(S) : F. Haviv and A. Patchornik It is certified that error appears in the above-identified patent and that said Letters Patent are hereby corrected as shown below:

ylthio)-7-" should read "-5-ylthio)methyl]-7-"; Table IX, 59th listing, 3rd column "-5-ylthio)-7-" should read "-5-ylthio)methyl]-7-". Table X, 13th listing, 1st column "-5-ylthio)-7-" should read "-5-ylthio)methyl]-7-"; Table X, 13th listing, 3rd column "-5-ylthio)-7-" should read "-5-ylthio)methyl]-7-"; Table X, 15th listing, 1st column "-5-ylthio)-7-" should read "-5-ylthio)methyl]-7-"; Table X, 15th listing, 3rd column "-5-ylthio)-7-" should read "-5-ylthio)methyl]-7-". Column 43, line 45 "pivalyoxybenzyl" should read "pivalyloxybenzyl"; Column 43, line 48 "dripwise" should read "dropwise"; Column 43, line 66-67 "3-(2-methyl-1,3,4-thiadiazol-5-ylthio)" should read "3-[(2-methyl-1,3,4-thiadiazol-5-ylthio)methyl]". Column 44, line 18 "3-(2-methyl-1,3,4-thiadiazol-5-ylthio)" should read "3-[(2-methyl-1,3,4-thiadiazol-5-ylthio)methyl]"; Column 44, line 27-28 "-5-ylthio)" should read "-5-ylthio)methyl]"; Column 44, line 55 "o-Isothioureamethylphenylacetic" should read "p-Isothioureamethylphenylacetic". Table XII, 6th listing, 1st column "-5-ylthio)" should read "-5-ylthio)methyl]"; Table XII, 6th listing, 3rd column "-5-ylthio)" should read "-5-ylthio)methyl]"; Table XII, 7th listing, 1st column "-5-ylthio)" should read "-5-ylthio)methyl]"; Table XII, 7th listing, 3rd column "-5-ylthio)" should read "-5-ylthio)methyl]"; Table XII, 9th listing, 1st column "-5-ylthio)" should read "-5-ylthio)methyl]"; Table XII, 9th listing, 3rd column "-5-ylthio)" should read "-4-ylthio)methyl]". Column 47, line 25 "-5-ylthio)" should read "-5-ylthio)methyl]". Column 48, line 26-27 "-5-ylthio)" should read "-5-ylthio)methyl]". Table XIII, 1st listing, 3rd column "-5-ylthio)" should read "-5-ylthio)methyl]"; Table XIII, 2nd listing,

UNITED STATES PATENT AND TRADEMARK OFFICE
CERTIFICATE OF CORRECTION

PATENT NO. : 3,994,875
DATED : November 30, 1976
INVENTOR(S) : F. Haviv and A. Patchornik It is certified that error appears in the above-identified patent and that said Letters Patent are hereby corrected as shown below:

3rd column "-5-ylthio)" should read "-5-ylthio)methyl]"; Table XIII, 3rd listing, 3rd column "-5-ylthio)" should read "-5-ylthio)methyl]"; Table XIII, 4th listing, 3rd column "-5-ylthio)-7-" should read "-5-ylthio)methyl]-7-"; Table XIII, 5th listing, 3rd column "-5-ylthio)-7-" should read "-5-ylthio)methyl]-7-"; Table XIII, 6th listing, 3rd column "-5-ylthio)-7-" should read "-5-ylthio)methyl]-7-"; Table XIII, 7th listing, 3rd column "-5-ylthio)-7-" should read "-5-ylthio)methyl]-7-"; Table XIII, 8th listing, 3rd column "-5-ylthio)-7-" should read "-5-ylthio)methyl]-7-". Column 49, line 11, "3-(2-methyl-1,3,4-thiadiazol-5-ylthio)-7-" should read "3-[(2-methyl-1,3,4-thiadiazol-5-ylthio)methyl]-7-"; line 13, "3-(1-methyltetrazol-5-ylthio)-7-" should read "3-[(1-methyltetrazol-5-ylthio)methyl]-7-"; line 21, "3-(2-methyl-1,3,4-thiadiazol-5-ylthio)-7-" should read "3-[(2-methyl-1,3,4-thiadiazol-5-ylthio)methyl]-7-"; line 23, "3-(1-methyltetrazol-5-ylthio)-7-" should read "3-[(1-methyltetrazol-5-ylthio)methyl]-7-"; line 34, "3-(2-methyl-1,3,4-thiadiazol-5-ylthio)-7-" should read "3-[(2-methyl-1,3,4-thiadiazol-5-ylthio)methyl]-7-"; line 37, "3-(1-methyltetrazol-5-ylthio)-7-" should read "3-[(1-methyltetrazol-5-ylthio)methyl]-7-".

Signed and Sealed this

Sixth Day of June 1978

[SEAL]

Attest:

RUTH C. MASON
Attesting Officer

DONALD W. BANNER
Commissioner of Patents and Trademarks